United States Patent
Porter et al.

(10) Patent No.: US 6,953,798 B1
(45) Date of Patent: Oct. 11, 2005

(54) β-ALANINE DERIVATES

(75) Inventors: John Robert Porter, Chinnor (GB); John Clifford Head, Maidenhead (GB); Graham John Warrellow, Northwood (GB); Sarah Catherine Archibald, Maidenhead (GB)

(73) Assignee: Celltech R&D Limited (GB)

( * ) Notice: Subject to any disclaimer, the term of this patent is extended or adjusted under 35 U.S.C. 154(b) by 301 days.

(21) Appl. No.: 09/450,999

(22) Filed: Nov. 29, 1999

(30) Foreign Application Priority Data

Nov. 30, 1998 (GB) .............................................. 9826174

(51) Int. Cl.$^7$ .................... C07D 403/12; C07D 401/12; A61K 31/53; A61K 31/444; A61P 19/10
(52) U.S. Cl. .................. 514/245; 514/255.05; 514/332; 514/335; 514/336; 514/338; 514/341; 514/342; 514/343; 544/212; 544/405; 546/261; 546/267; 546/268.7; 546/269.1; 546/269.7; 546/275.4; 546/282.1; 546/323
(58) Field of Search ............................ 514/255.05, 332, 514/335, 336, 338, 341, 342, 343; 544/405; 546/261, 267, 268.7, 269.1, 269.7, 275.4, 278.4, 282.1, 323

(56) References Cited

U.S. PATENT DOCUMENTS

| | | | |
|---|---|---|---|
| 4,470,973 A | | 9/1984 | Natarajan et al. ............ 424/177 |
| 4,554,273 A | * | 11/1985 | Bayssat et al. .............. 514/221 |
| 4,987,132 A | | 1/1991 | Mase et al. .................. 514/252 |
| 5,164,372 A | | 11/1992 | Matsuo et al. ................. 514/19 |
| 5,227,490 A | | 7/1993 | Hartman et al. ............. 514/317 |
| 5,260,277 A | | 11/1993 | McKenzie .................... 544/18 |
| 5,296,486 A | | 3/1994 | Lazer et al. ................. 514/333 |
| 5,399,585 A | | 3/1995 | Alig et al. ................... 514/438 |
| 5,510,346 A | * | 4/1996 | Martin et al. ................ 514/221 |
| 5,698,691 A | * | 12/1997 | Yukimasa et al. ........... 540/490 |
| 5,773,646 A | | 6/1998 | Clare et al. .................. 241/439 |
| 6,093,696 A | | 7/2000 | Head et al. .................... 514/19 |
| 6,096,773 A | * | 8/2000 | Scott et al. .................. 514/382 |
| 6,100,282 A | * | 8/2000 | Alig et al. .................... 514/371 |
| 6,291,503 B1 | * | 9/2001 | Schoop et al. ............... 514/401 |

FOREIGN PATENT DOCUMENTS

| | | |
|---|---|---|
| DE | 23 16 881 A | 10/1973 |
| DE | 196 54 483 A | 1/1998 |
| EP | 0 031 104 A1 | 7/1981 |
| EP | 0 048 763 A1 | 4/1982 |
| EP | 0 144 230 A | 6/1985 |
| EP | 0 288 176 A | 10/1988 |
| EP | 0 322 068 A1 | 6/1989 |
| EP | 0 394 989 A2 | 10/1990 |
| EP | 0 498 268 A2 | 8/1992 |
| EP | 0 596 406 A1 | 5/1994 |
| EP | 0 710 657 A1 | 5/1996 |
| EP | 0 710 659 A1 | 5/1996 |
| EP | 0 842 943 A2 | 5/1998 |
| EP | 0 842 945 A2 | 5/1998 |
| JP | 56 090045 | 7/1981 |
| JP | 03 135962 | 6/1991 |
| WO | WO 86/02353 | 4/1986 |
| WO | WO 93/00095 | 1/1993 |
| WO | WO 93/08174 | 4/1993 |
| WO | WO 93/09795 | 5/1993 |
| WO | WO 94/15954 | 7/1994 |
| WO | WO 94/15955 | 7/1994 |
| WO | WO 94/29285 | 12/1994 |
| WO | WO 95/13811 | 5/1995 |
| WO | WO 95/15973 | 6/1995 |
| WO | WO 95/19356 | 7/1995 |
| WO | WO 95/35314 | 12/1995 |
| WO | WO 96/01644 | 1/1996 |
| WO | WO 96/22966 | 8/1996 |
| WO | WO 96/26190 | 8/1996 |
| WO | WO 97/03094 | 1/1997 |
| WO | WO 97/04247 | 2/1997 |
| WO | WO 97/08145 | 3/1997 |
| WO | WO 97/12866 | 4/1997 |
| WO | WO 97/23480 | 7/1997 |
| WO | WO 97/24124 | 7/1997 |
| WO | WO 97/31907 | 9/1997 |
| WO | WO 97/36858 | 10/1997 |
| WO | WO 97/36859 | 10/1997 |
| WO | WO 97/36861 | 10/1997 |
| WO | WO 97/36862 | 10/1997 |
| WO | WO 97/44333 | 11/1997 |
| WO | WO 98/00395 | 1/1998 |
| WO | WO 98/04247 | 2/1998 |
| WO | WO 98/04913 | 2/1998 |
| WO | WO 98/18460 | 5/1998 |
| WO | WO 98/25892 | 6/1998 |
| WO | WO 98/31359 | 7/1998 |

(Continued)

OTHER PUBLICATIONS

Hawley, Gessner, "The Condensed Chemical Dictonary", 1977, Van Nostrand, New York, p. 436 & 822.*
Kato, Shinji; Hamada, Yasumasa; Shioiri, Takayuki, Tetrahedron Lett., 29(49), 6465–6 (English) 1988.*

(Continued)

*Primary Examiner*—Thomas C. McKenzie
(74) *Attorney, Agent, or Firm*—Woodcock Washburn LLP

(57) ABSTRACT

Alkanoic acid derivatives of formula (1) are described:

$$Ar^1(Alk^a)_rL^1Ar^2CH(R^1)C(R^a)(R^{a'})R \quad (1)$$

$Ar^1$ is an optionally substituted aromatic or heteroarotic group;
$L^1$ is a covalent bond or a linker atom or group;
$Ar^2$ is an optionally substituted phenylene or nitrogen-containing six-membered heteroarylene group;
R is a carboxylic acid (—$CO_2H$) or a derivative thereof;
and the salts, solvates, hydrates and N-oxides thereof.

The compounds are able to inhibit the binding of α4 integrins to their ligands and are of use in the prophylaxis and treatment of immune or inflammatory disorders.

20 Claims, No Drawings

FOREIGN PATENT DOCUMENTS

| | | |
|---|---|---|
| WO | WO 98/42662 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | WO 98/58902 | 12/1998 |
| WO | WO 99/06390 | 2/1999 |
| WO | WO 99/06431 | 2/1999 |
| WO | WO 99/06432 | 2/1999 |
| WO | WO 99/06433 | 2/1999 |
| WO | WO 99/06434 | 2/1999 |
| WO | WO 99/06435 | 2/1999 |
| WO | WO 99/06436 | 2/1999 |
| WO | WO 99/06437 | 2/1999 |
| WO | WO 99/10312 | 3/1999 |
| WO | WO 99/10313 | 3/1999 |
| WO | WO 99/20272 | 4/1999 |
| WO | WO-99/23063 A1 * | 5/1999 |
| WO | WO 99/26921 | 6/1999 |
| WO | WO 99/26922 | 6/1999 |
| WO | WO 99/26945 | 6/1999 |
| WO | WO 99/30709 | 6/1999 |
| WO | WO 99/31061 | 6/1999 |
| WO | WO 99/31099 | 6/1999 |
| WO | WO 99/32457 | 7/1999 |
| WO | WO 99/35163 | 7/1999 |
| WO | WO 99/36393 | 7/1999 |
| WO | WO 99/37618 | 7/1999 |
| WO | WO 99/43642 | 9/1999 |
| WO | WO 99/44994 | 9/1999 |
| WO | WO 99/48879 | 9/1999 |
| WO | WO 99/52879 | 10/1999 |
| WO | WO 99/52896 | 10/1999 |
| WO | WO 99/52898 | 10/1999 |
| WO | WO 99/60015 | 11/1999 |
| WO | WO 99/61465 | 12/1999 |
| WO | WO 99/64395 | 12/1999 |
| WO | WO 99/67230 | 12/1999 |
| WO | WO 00/00486 | 1/2000 |
| WO | WO 00/01383 | 1/2000 |
| WO | WO 00/06169 | 2/2000 |
| WO | WO 00/07544 | 2/2000 |
| WO | WO 00/17197 | 3/2000 |
| WO | WO 00/23419 | 4/2000 |
| WO | WO 00/31067 | 6/2000 |
| WO | WO 00/35855 | 6/2000 |
| WO | WO-00/41469 A1 * | 7/2000 |

OTHER PUBLICATIONS

Suvorov, N.N. et al, Zhur. Obsh. Khim., 30, 2051–5, 1960, cited in Chemical Abstracts, vol. 55, 6431c–f, 1961.*

Rodioniv, V.M. et al, Zhur. Obsh. Khim., 27, 2234–8, 1957, cited in Chemical Abstracts, vol. 52, 6260b–e, 1958.*

Wasserman, Harry H.; Robinson, Ralph P.; Carter, Charles G., J. Am. Chem. Soc., 105(6), 1697–8 (English) 1983.*

Mamaev, V.P., Zh.Obshch.Khim., 27, 1957, 1290–3, (English trans p 1376), 1957, cited in Chemical Abstracts, vol. 52, 2748c–e, 1958.*

Noseworthy, J.H., Nature, vol. 399, 1999, supp., pp. A40–47.*

Noseworthy, J.H. et al, Curr. Opin. Neurology, 12, 1999, 279–293.*

Hawley, Gessner, The Condensed Chemical Distionary, 1997, Van Nostrand, New York, pp. 25 & 436.*

Narisada, Masayuki; Nagata, Wataru DE 2837264 Jan. 3, 1979 Chemical Abstracts 1979:420520.*

Alhaique, F., et al., "Cyclisation of dinitriles by sodium alkoxides a new synthesis of naphthyridines," *Tetrahedron Letters*, 1975, 3, 173–174.

Ames, D.E., et al., "Condensation of β–dicarbonyl compounds with halogenopyridinecarb–oxylic acids. A convenient synthesis of some naphthyridine derivatives," *J.C.S. Perkin I*, 1972, 705–710.

Bodor, N., "Novel approaches in prodrug design," *Alfred Benzon Symposium*, 1982, 17, 156–177.

Brooks, Peter C., et al., "Antiintegrin αvβ3 blocks human breast cancer growth and angiogenesis in human skin," *J. Clin. Invest.*, 1995, 96, 1815–1822.

Davies, S..G., et al., "Asymmetric synthesis of R–β–amino butanoic acid and S–β–tyrosine: homochiral lithium amide equivalents for Michael additions toα,β–unsaturated esters," *Tetra. Asymmetry*, 1991, 2(3), 183–186.

Erle, D.J., et al., "Expression and function of the Mad-CAM–1 receptor, integrin α4β7, on human leukocytes," *J. Immunol.*, 1994, 153, 517–528.

Giacomello, et al., "Synthesis of 2,6–naphthyridine," *Tetra. Letters*, 1965, 16, 1117–1121.

Hammes, H., et al., "Subcutaneous injection of a cyclic peptide antagonist of vitronectin receptor–type integrins inhibits retinal neovascularization," *Nature Medicine*, 1996, 2, 529–533.

Hodivala–Dilke, K.M., "β3–integrin–deficient mice are a model for glanzmann thrombasthenia showing placental defects and reduced survival," *J. Clin. Invest.*, 1999, 103(2), 229–238.

Kalvin, D.M., et al., Synthesis of (4R)–D,L–[4$^2$H]– and (4S)–D,L–[4–$^2$H] homoserine lactones, *J. Org. Chem.*, 1985, 50, 2259–2263.

Koivunen, E., et al., "Selection of peptides binding to the α$_5$β$_1$ integrin from phage display library," *J. Biological Chemistry*, 1993, 268(27), 20205–20210.

Mitjans, F., et al., "An anti–αv–integrin antibody that blocks integrin function inhibits the development of a human melanoma in nude mice," *J. Cell Science*, 1995, 108, 2825–2838.

Molina, P., et al., "Iminophosphorane–mediated annelation of a pyridine ring into a preformed pyridine one: synthesis of naphthyridine, pyrido [1,2–c] pyrimidine and pyrido [1,2–c] quinazoline derivatives," *Tetrahedron*, 1992, 48(22), 4601–4616.

Newham, P., et al., "Integrin adhesion receptors: structure, function and implications for biomedicine," *Nolecular Medicine Today*, 1996, 304–313.

Numata, A., et al., "General synthetic method for naphthyridines and their N–oxides containing isoquinolinic nitrogen," *Synthesis*, 1999, 2, 306–311.

Sakamoto, T., et al., "Condensed heteroaromatic ring systems. III. synthesis of naphthyridine derivatives by cyclization of ethynylpyridinecarboxamides," *Chem. Pharm. Bull.* 1985, 33(2), 626–633.

Singh, G., et al., "Prodrug approach in new drug design and development," *J. Sci. Ind. Res.*, 1996, 55, 497–510.

Srivatsa, S.S., et al., "Selective αvβ3 integrin blockade potently limits neointimal hyperplasia and lumen stenosis following deep coronary arterial stent injury: evidence for the functional importance of integrin αvβ3 and osteopontin expression during neointima formation," *Cariovascular Research*, 1997, 36, 408–428.

Stupack, D.G., et al., "induction of $\alpha_v B_3$ integrin–mediated attachment to extracellular matrix in $\beta_1$ integrin (CD29)–negative B cell lines," *Experi. Cell Research*, 1992, 203, 443–448.

Tan R., et al., "Synthesis of 2, 6–naphthyridine and some of its derivatives," *Tetrahedron Letters*, 1965, 31, 2737–2744.

Rico, J.G., et al., "A highly steroselective michael addition to an $\alpha\beta$–unsaturated ester as the crucial step in the synthesis of a novel $\beta$–amino acid–containing fibrinogen receptor antagonist," *J. Org. Chem.*, 1993, 58, 7948–7951.

Zablocki, J.A., "Potent in vitroand in vivo inhibitors of platelet aggregation based upon the arg–gly–asp sequence of fibrinogen. (Aminobenzamidino)succinyl (ABAS) series of orally active fibrinogen receptor antagonists," *J. Med. Chem.*, 1995, 38, 2378–2394.

Hammadi, A., et al., "Diastereoselective hydrogenation of monodehydro enkephalins conrolled by chiral rhodium catalysts," *Tetrahedron: Asymmetry*, 1992, 3(10), XP002106601, 1247–1262.

Nunami, K., et al., "A novel synthesis of methyl 1,5–disubstituted imidazole–4–carboxylates using 3–bromo–2–isocyanoacrylates," *J. Org. Chem.*, 1994, 59, XP002106602, 7635–7642.

Shimohigashi, Y., et al., "Dehydro–enkephalins," *Int. J. Peptide Protein Res.*, 1983, 21, XP002106600, 202–208.

Strange, P.G., et al., "Studies of enzyme–mediated reactions. Part II. Stereochemistry of the elimination of ammonia form L–tyrosine catalysed by the enzyme from maize," *J. Chem. Soc., Perkin I*, 1972, 18, XP002106603, 2364–2372.

WPI/Derwent No. XP002106604, Japanese Patent No. JP 60 190749 (Mitsui Toatsu Chem. Inc.), Sep. 28, 1985, 1 page, Abstract only.

Clausen, K., et al., "Studies on amino acids and peptides. II. Synthesis of protected endothiodipeptides," *J. Chem. Scr.*, 1982, 20(1–2), 14–18, doc. No. 97:163474 (abstract only, 1 page).

Frank, R., et al., "Extremely mild reagent for Boc deprotection," *J. Chem. Commun. (Cambridge)*, 1996, 22, 2509–2510, doc. No. 126:104395 (abstract only, 3 pages).

Kobayashi, A., et al., "Syntheses of 2–dialkylamino–4, 4–disubstituted 5 (4H)–thiazolones," *J. Yakugaku Zasshi*, 1970, 90(11), 1377–1380, doc. No. 74:31713 (abstract only, 3 pages).

Koenig, H.B., et al., ".beta.–Lactam antibiotics," *Ger. Offen.*, 41 pages, doc. No. 83:97276 (abstract only, 5 pages).

Masuda, T., *Jpn. Kodai Tokkyo Koho*, 22 pages, doc. No. 115:280022 (abstract only, 1 page).

Pfeifer, T., et al., "Specific fragmentation of thioxo peptides facilitates the assignment of the thioxylated amino acid," *J. Mass Spectrom*, 1997, 32(10), 1064–1071, doc. No. 127:331738 (abstract only 2 pages).

Sawa, N., et al., "Preparation of 4(5)–thiocarbamoylimidazole compounds," *Jpn. Kokai Tokkyo Koho*, 33 pages, doc. No. 115:183296 (abstract only, 2 pages).

Schutkowski, M., et al., "Inhibition of peptidyl–prolyl cis/trans isomerase activity by substrate analog structures: thioxo tetrapeptide–4–nitroanilides," *Biochemistry*, 1995, 84(40), 13016–13026, doc. No. 123:221511 (abstract only, 4 pages).

"Cephalosporins," *Jpn. Kokai Tokkyo Koho*, 40 pages, doc. No. 99:5433 (abstract only, 2 pages).

Lobb, R.R., et al., "Small molecule antagonists of alpha4 integrins: novel drugs for asthma," *Exp. Opin, Invest. Drugs*, 1999, XP000885957, 8(7), 935–945.

Samanen, J., et al., "Vascular indications for integrin alpha V antagonists," *Current Pharm. Design.*, 1997, 3, 545–584.

Šavrda, J., "CIS–TRANS isomerism of N–ACYL derivatives of proline and its analogues, linear peptides with CIS peptide bonds," *Proc. 14$^{th}$ European Peptide Symposium*, Loffet, A. (ed.), 1976, 653–656.

Azzouny, A.E., et al., "Synthesis of some N–substituted salicylamides structurally related to certain antimicrobials," *Pharmazie*, 1977, 32(6), 318–323 (abstract).

Badshah, A., et al., "Catalytic reduction of azlactones in alkaline media. Synthesis of amino acids," *J. of Organic Chemistry*, 1972, 37(18), 2916–2918.

Tous, G., et al., "O'–(Epoxyalkyl) tyrosines and (Epoxyalkyl) phenylalanine as irreversible inactivators of serine proteases: synthesis and inhibition mechanism," *J. of Medicinal Chemistry*, 1990, 33(6), 1620–1634.

Buckle, D.R., et al., "Non Thiazolidinedione Antihyperglycaemic Agents. 1: $\alpha$–Heteroatom Substituted $\beta$–Phenylpropanoic Acids," *Bioorg. Med. Chem. Lett.*, 1996, 6(17), 2121–2126.

Keenan, R.M. et al., "Discovery of Potent Nonpeptide Vitronectin Receptor (av$\beta_3$) Antagonists," *J. Med. Chem.*, 1997, 40(15), 2289–2292.

McDowell, R.S. et al., "From Peptide to Non–Peptide. 2. The de Novo Design of Potent, Non–Peptidal Inhibitors of Platelet Aggregation Based on a Benzodiazepinedione Scaffold," *J. Am. Chem. Soc.*, 1994, 116, 5077–5083.

Miller, W.H. et al., "Structure–Activity Relationships in 8–Oxo–1,4–Benzodiazepine–2–Acetic Acid GPIIb/IIIa Antagonists. The 2–Benzazepine Series," *Bioorg. Med. Chem. Lett.*, 1996, 6(21), 2481–2486.

Ukai, Y. et al., "A novel synthetic inhibitor of endopeptidase–24.15," *Chemical Abstracts*, 1997, 127(2), 1 page.

Venturella, V.S. et al., "Substituted 1,3–Dihydro–4H–furo [3,4–d]–1,3–benzodiazepin–3–ones: Synthesis and Scope of the Method," *J. Heterocyclic Chem.*, 1969, 6(5), 671–679.

Wojciechowska, H. et al., "Preparation of 2,4–dinitrophenyl derivatives of tyrosine," *Chemical Abstracts*, 1968, 68(25), Abstract No. 114926r, 1 page.

Abraham, W.M. et al., "$\alpha_4$–Integrins Mediate Antigen–Induced Late Bronchial Responses and Prolonged Airway Hyperresponsiveness in Sheep," *J. Clin. Invest.*, 1994, 93, 776–787.

Bach et al., "Anomalous optical rotation and circular dichroism of N–thioacylated.alpha.–amino acids and deriva," *Acta Chem. Scand.*, 1966, 20(10), 2781–2794.

Barrett, G.C., "Circular dichroism of N–thiobenzoly–1–$\alpha$–amino acids. III. Their circular dichroism through the near–ultraviolet wavelength range," *J. Chem. Soc.*, 1967, Section C, 1–5.

Berlin, C. et al., "$\alpha 4\beta 7$ Integrin Mediates Lymphocyte Binding to the Mucosal Vascular Addressin MAdCAM–1," *Cell*, 1993, 74, 185–195.

Binns, R.M. et al., "The Role of E–Selectin in Lymphocyte and Polymorphonuclear Cell Recruitment into Cutaneous Delayed Hypersensitivity Reactions in Sensitized Pigs," *J. Immunol.*, 1996, 157, 4094–4099.

Briskin, M.J. et al., "Structural Requirements for Mucosal Vascular Addressin Binding to Its Lymphocyte Receptor $\alpha_4\beta_7$," *J. Immunol.*, 1996, 156, 719–726.

Cardarelli, P.M. et al., "Cyclic RGD Peptide Inhibits $\alpha 4\beta 7$ Interaction with Connecting Segment 1 and Vascular Cell Adhesion Molecule," *J. Biol. Chem.*, 1994, 269(28), 18668–18673.

Chemical Abstracts, "N–[4–Thiazolidinyol)carbonyl]amino acid derivatives," 1981, 95(19), Abstract No. 169173f, 1 page.

Corey, E.J. et al., "A Synthetic Method for Formyl → Ethynyl Conversion (RCHO → RC≅CH or RC≅CR')," Tetrahedron Lett., 1972, 36, 3769–3772.

Cornforth, J.W., "Oxazoles and Oxazolones," Chem. Penicillin, Princeton Book Review, 1949, pp. 688–799, and 800.

Ferguson, T.A. et al., "Two integrin–binding peptides abrogate T cell–mediated immune responses in vivo," Proc. Natl. Acad. Sci. USA, 1991, 88, 8072–8076.

Fu, H. et al., "Preliminary study on synthesis and antitumor activity in vitro of derivatives of timonacic," Chemicals Abstracts, 1988, 108(17), Abstract No. 150358k, 1 page.

Harris, R.L.N. et al., Aust. J. Chem., "Potential wool growth inhibitors. 2(1H)–Pyridone analogs of mimosine," 1977, 30(3), 649–655.

Hartke, K. et al., "Dithio and thiono esters. Part 61. Synthesis of α–amino dithioesters and endothipdipeptides,", J. Prakt. Chem., 1996, 338(3), 251–256.

Holzmann, B. et al., "Peyer's patch–specific lymphocyte homing receptors consist of a VLA–4–like α chain associated with either of two integrin α chains, one of which is novel," EMBO J., 1989, 8)6), 1735–1741.

Humphries, M.J. et al., "Mechanisms of VCAM–1 and fibronectin binding to integrin $\alpha_4\beta_1$: implications for integrin function and rational drug design," Ciba Foundation Symposium, 1995, 189, 177–194.

Issekutz, T.B., "Inhibition of Lymphocyte Endothelial Adhesion and In Vivo Lymphocyte Migration to Cutaneous Inflammation by TA–3, a New Monoclonal Antibody to Rat LFA–1," J. Immunol., 1992, 149(10), 3394–3402.

Jaynes, B.H. et al., "Synthesis and In Vivo Antibacterial Activity of Hygromycin a Analogs Modified at the $C_4$' Aryl Position," Bioorg. Med. Chem. Letts., 1993, 3(8), 1531–1536.

Jepson, J.B. et al., "Reactions of α–Thioacylamino–acids. Their conversion into Thiazolones and Derivatives Thereof," J. Chem. Soc., 1955, 1791–1797.

Lei, H. et al., "Efficient Synthesis of a Phosphinate Bis–Amino Acid and Its Use in the Construction of Amphiphilic Peptides," J. Org. Chem., 1994, 59, 4206–4210.

Li Z. et al., "Effect of an anti–Mo1 MAb on ozone–induced airway inflammation and airway hyperresponsiveness in dogs," Am. J. Physiol., 1992, 263(6 Pt 1), L723–726.

Marlin, S.D. et al., "LFA–1 Immunodeficiency Disease," J. Exp. Med., 1986, 164, 855–867.

Masahiko, N., Japanese Patent No. 57–080370 published May 19, 1982, "Alpha–Methylcinnamic Acid Derivative, its Preparation and Antilipemic Agent Containing The Same," Patent Abstracts of Japan, 1982, 1 page.

Nagasawa, H.T. et al., "β–Substituted Cysteines as Sequestering Agents for Ethanol–Derived Acetaldehyde in Vivo," J. Med. Chem., 1987, 30, 1373–1378.

Noike, Y., "Synthesis of Quinolizine Derivatives. VI. Synthesis of 3–Aminoquinolizines. (1). Synthesis of dl–3–Amino–, dl–3–epi–Amino–, and dl–3–epi–Dimethylaminoquinolizidines," Yakugaku Zasshi, 1959, 79(12), 1514–1518 (English summary included).

Ohki, S. et al., "Synthesis of quinolizine derivatives. V. Studies on Diastereoisomer of Ethyl 3–Quinolizidinecarboxylate," Chem. Pharm. Bull., 1959, 7(6), 708–712.

Osborne, L., "Leukocyte Adhesion to Endothelium in Inflammation," Cell, 1990, 62, 3–6.

Osborn, L. et al., "Direct Expression Cloning of Vascular Cell Adhesion Molecule 1, a Cytokine–Induced Endothelial Protein that Binds to Lymphocytes," Cell, 1989, 59, 1203–1211.

Podolsky, D.K. et al., "Attenuation of Colitis in the Cotton–top Tamarin by Anti–α4 integrin Monoclonal Antibody," J. Clin. Invest., 1993, 92, 372–380.

Schultz, Von O.–E. et al., "Analogs of nuleic acid based as antimetabolites," Arzneimittel Forschung. Drug Res., 1967, 17(8), 1060–1064 (English summary included).

Shroff, H.N. et al., "Small Peptide Inhibitors of $\alpha_4\beta_7$ Mediated MAdCAM–1 Adhesion to Lymphocytes," Barge. Med. Chem. Letts., 1996, 6(21), 2495–2500.

Sonnenberg, A., "Integrins and Their Ligands," Curr. Topics Microbiol. Immunol., 1993, 184, 7–35.

Springer, T.A., "Adhesion receptors of the immune system," Nature, 1990, 346, 425–434.

Springer, T.A., "Traffic Signals for Lymphocyte Recirculation and Leukocyte Emigration: The Multistep Paradigm," Cell, 1994, 76, 301–314.

Tsunematsu, H. et al., "Hydrolysis of phenylthiazolones of p–guanidinophenylalanine and arginine by trypsin and related enzymes," J. Biochem., 1983, 94(4), 1119–1125.

Vanderslice, P. et al., "A Cyclic Hexapeptide is a Potent Antagonist of α4 Integrins," J. Immunol., 1997, 158, 1710–1718.

Yanagisawa, H. et al., WO 97/37970, "Preparation of phenylalkylcarboxylic acid derivatives lowering blood sugar level," Chemical Abstracts, 1997, Abstract 127:307307, 4 pages.

Yang, X., "A predominant role of integrin α4 in the spontaneous development of autoimmune diabetes in nonobese diabetic mice," Proc. Natl. Acad. Sci. USA, 1994, 91, 12604–12608.

Yednock, T.A., "Prevention of experimental autoimmune enoephalomyelitis by antibodies against α4β1 integrin," Nature, 1992, 356, 63–66.

Whitlock, B.J. et al., "Structure and synthesis of lathyrine," J. Org. Chem., 1965, 30, 115–118.

WPI / Derwent No. XP–002076854, Japanese Patent No. JP 04 193 895 A (Ajinomoto, K.K.), Jul. 13, 1992, DW9234, 1 Page, Abstract Only.

WPI / Derwent No. XP–002076855, Japanese Patent No. JP 56 049 373 A (Dainippon Pharm Co Ltd), May 2, 1981, DW8125, 1 Page, Abstract Only.

\* cited by examiner

β-ALANINE DERIVATES

This invention relates to a series of alkanoic acid derivatives, to processes for their preparation, and to their use in medicine.

Over the last few years it has become increasingly clear that the physical interaction of inflammatory leukocytes with each other and other cells of the body plays an important role in regulating immune and inflammatory responses [Springer, T A. Nature, 346, 425, (1990); Springer, T. A. Cell 76, 301, (1994)]. Many of these interactions are mediated by specific cell surface molecules collectively referred to as cell adhesion molecules.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 14 different integrin alpha chains and 8 different integrin beta chains have been identified [Sonnenberg, A. Current Topics in Microbiology and Immunology, 184, 7, (1993)]. The members of the family are typically named according to their heterodimer composition although trivial nomenclature is widespread in this field. Thus the integrin termed α4β1 consists of the integrin alpha 4 chain associated with the integrin beta 1 chain, but is also widely referred to as Very Late Antigen 4 or VLA4. Not all of the potential pairings of integrin alpha and beta chains have yet been observed in nature and the integrin family has been subdivided into a number of subgroups based on the pairings that have been recognised [Sonnenberg, A. ibid].

The importance of cell adhesion molecules in human leukocyte function has been further highlighted by a genetic deficiency disease called Leukocyte Adhesion Deficiency (LAD) in which one of the families of leukocyte integrins is not expressed [Marlin, S. D. et al J. Exp. Med. 164, 855 (1986)]. Patients with this disease have a reduced ability to recruit leukocytes to inflammatory sites and suffer recurrent infections which in extreme cases may be fatal.

The potential to modify adhesion molecule function in such a way as to beneficially modulate immune and inflammatory responses has been extensively investigated in animal models using specific monoclonal antibodies that block various functions of these molecules [e.g. Issekutz, T. B. J. Immunol. 3394, (1992); Li, Z. et al Am. J. Physiol. 263, L723, (1992); Binns, R. M. et al J. Immunol. 157, 4094, (1996)]. A number of monoclonal antibodies which block adhesion molecule function are currently being investigated for their therapeutic potential in human disease.

One particular integrin subgroup of interest involves the α4 chain which can pair with two different beta chains β1 and β7 [Sonnenberg, A. ibid]. The α4β1 pairing occurs on many circulating leukocytes (for example lymphocytes, monocytes and eosinophils) although it is absent or only present at low levels on circulating neutrophils. α4β1 binds to an adhesion molecule (Vascular Cell Adhesion Molecule-1 also known as VCAM-1) frequently up-regulated on endothelial cells at sites of inflammation [Osborne, L. Cell, 62, 3, (1990)]. The molecule has also been shown to bind to at least three sites in the matrix molecule fibronectin [Humphries, M. J. et al. Ciba Foundation Symposium, 189, 177, (1995)]. Based on data obtained with monoclonal antibodies in animal models it is believed that the interaction between α4β1 and ligands on other cells and the extracellular matrix plays an important role in leukocyte migration and activation [Yednock, T. A. et al, Nature, 356, 63, (1992); Podolsky, D. K. et al. J. Clin. Invest. 92, 373, (1993); Abraham, W. M. et al. J. Clin. Invest. 93, 776, (1994)].

The integrin generated by the pairing of α4 and β7 has been termed LPAM-1 [Holzmann, B and Weissman, I. EMBO J. 8, 1735, (1989)] and like α4β1, binds to VCAM-1 and fibronectin. In addition, α4β7 binds to an adhesion molecule believed to be involved in the homing of leukocytes to mucosal tissue termed MAdCAM-1 [Berlin, C. et al, Cell, 74, 185, (1993)]. The interaction between α4β7 and MAdCAM-1 may also be important at sites of inflammation outside of mucosal tissue [Yang, X-D. et al, PNAS, 91, 12604 (1994)].

Regions of the peptide sequence recognised by α4β1 and α4β7 when they bind to their ligands have been identified. α4β1 seems to recognise LDV, IDA or REDV peptide sequences in fibronectin and a QIDSP sequence in VCAM-1 [Humphries, M. J. et al, ibid] whilst α4β7 recognises a LDT sequence in MAdCAM-1 [Briskin, M. J. et al, J. Immunol. 156, 719, (1996)]. There have been several reports of inhibitors of these interactions being designed from modifications of these short peptide sequences [Cardarelli, P. M. et al J. Biol. Chem. 269, 18668, (1994); Shroff, H. N. Bioorganic. Med. Chem. Lett. 6, 2495, (1996); Vanderslice, P. J. Immunol. 158, 1710, (1997)]. It has also been reported that a short peptide sequence derived from the α4β1 binding site in fibronectin can inhibit a contact hypersensitivity reaction in a trinitrochlorobenzene sensitised mouse [Ferguson, T. A. et al, PNAS 88, 8072, (1991)].

Since the alpha 4 subgroup of integrins are predominantly expressed on leukocytes their inhibition can be expected to be beneficial in a number of immune or inflammatory disease states. However, because of the ubiquitous distribution and wide range of functions performed by other members of the integrin family it is very important to be able to identify selective inhibitors of the alpha 4 subgroup.

We have now found a group of compounds which are potent and selective inhibitors of α4 integrins. Members of the group are able to inhibit α4 integrins such as α4β1 and/or α4β7 at concentrations at which they generally have no or minimal inhibitory action on a integrins of other subgroups. The compounds are thus of use in medicine, for example in the prophylaxis and treatment of immune or inflammatory disorders as described hereinafter.

Thus according to one aspect of the invention we provide a compound of formula (1):

$$Ar^1(Alk^a)_xL^1Ar^2CH(R^1)C(R^a)(R^{a'})R \quad (1)$$

wherein

Ar$^1$ is an optionally substituted aromatic or heteroaromatic group;

L$^1$ is a covalent bond or a linker atom or group selected from —CON(R$^2$)— [where R$^2$ is a hydrogen atom or a C$_{1-3}$alkyl group], —SO$_2$N(R$^2$)—, —C(O)O—, —N(R$^2$)— or —O—;

Ar$^2$ is an optionally substituted phenylene or nitrogen-containing six-membered heteroarylene group;

R$^1$ is a group selected from —NHCOR$^3$ [where R$^3$ is an optionally substituted aliphatic, heteroaliphatic, cycloaliphatic, polycycloaliphatic, heterocycloaliphatic, heteropolycycloaliphatic, aromatic or heteroaromatic group], —NHSO$_2$R$^3$, —NHR$^3$, —NHC(O)OR$^3$, —NHCSR$^3$, —NHCON(R$^3$)(R$^{3a}$) [where R$^{3a}$ is a hydrogen atom or a group R$^3$ and R$^3$ and R$^{3a}$ are the same or different], —NHSO$_2$N(R$^3$)(R$^{3a}$), —NHCSN(R$^3$)(R$^{3a}$), —CON(R$^3$)(R$^{3a}$) or —CSN(R$^3$)(R$^{3a}$);

R$^a$ and R$^{a'}$ which may be the same or different is each independently selected from a hydrogen or halogen atom or an optionally substituted straight or branched alkyl, alkenyl or alkynyl, haloalkyl, alkoxy, haloalkoxy, alkylthio, or -$(Alk^b)_m R^b$ group (in which $Alk^b$ is a $C_{1-3}$alkylene chain, m is zero or the integer 1 and $R^b$ is a —OH, —SH, —NO$_2$, —CN, —CO$_2$H, —CO$_2$R$^c$, (where R$^c$ is an optionally substituted straight or branched $C_{1-6}$alkyl group), —SO$_3$H, —SOR$^c$, —SO$_2$R$^c$, —SO$_3$R$^c$, —OCO$_2$R$^c$, —C(O)H, —C(O)R$^c$, —OC(O)R$^c$, —C(S) R$^c$, —NR$^d$R$^e$ [where R$^d$ and R$^e$ which may be the same or different is each a hydrogen atom or an optionally substituted straight or branched alkyl group], —C(O)N (R$^d$)(R$^e$), —OC(O)N(R$^d$)(R$^e$), —N(R$^d$)C(O)R$^e$, —CSN (R$^d$)(R$^e$), —N(R)$^d$C(S)R$^e$, —SO$_2$N(R$^d$)(R$^e$), —N(R$^d$) SO$_2$R$^e$, —N(R$^d$)CON(R$^e$)(R$^f$) [where R$^f$ is a hydrogen atom or an optionally substituted straight or branched alkyl group], —N(R$^d$)C(S)N(R$^e$)(R$^f$) or —N(R$^d$)SO$_2$N (R$^e$)(R$^f$) group).

Alk$^a$ is an optionally substituted aliphatic or heteroaliphatic chain;

r is zero or the integer 1;

R is a carboxylic acid (—CO$_2$H) or a derivative thereof;

and the salts, solvates, hydrates and N-oxides thereof.

It will be appreciated that compounds of formula (1) may have one or more chiral centres, and exist as enantiomers or diastereomers. The invention is to be understood to extend to all such enantiomers, diastereomers and mixtures thereof, including racemates. Formula (1) and the formulae hereinafter are intended to represent all individual isomers and mixtures thereof, unless stated or shown otherwise.

In the compounds of the invention as represented by formula (1) and the more detailed description hereinafter certain of the general terms used in relation to substituents are to be understood to include the following atoms or groups unless specified otherwise.

Thus as used herein the term "straight or branched alkyl", whether present as a group or part of a group includes straight or branched $C_{1-6}$alkyl groups, for example $C_{1-4}$alkyl groups such as methyl, ethyl, n-propyl, i-propyl or t-butyl groups. Similarly, the terms "straight or branched alkenyl" or "straight or branched alkynyl" are intended to mean $C_{2-6}$alkenyl or $C_{2-6}$alkynyl groups such as $C_{2-4}$alkenyl or $C_{2-4}$alkynyl groups.

The term "halogen atom" is intended to include fluorine, chlorine, bromine or iodine atoms.

The term "straight or branched haloalkyl" is intended to include the alkyl groups just mentioned substituted by one, two or three of the halogen atoms just described. Particular examples of such groups include —CF$_3$, —CCl$_3$, —CHF$_2$—CHCl$_2$, —CH$_2$F, and —CH$_2$Cl groups.

The term "straight or branched alkoxy" as used herein is intended to include straight or branched $C_{1-6}$alkoxy e.g. $C_{1-4}$alkoxy such as methoxy, ethoxy, n-propoxy, i-propoxy and t-butoxy. "Haloalkoxy" as used herein includes any of those alkoxy groups substituent by one, two or three halogen atoms as described above. Particular examples include —OCF$_3$, —OCCl$_3$, —OCHF$_2$, —OCHCl$_2$, —OCH$_2$F and —OCH$_2$Cl groups.

As used herein the term "straight or branched alkylthio" is intended to include straight or branched $C_{1-6}$alkylthio, e.g. $C_{1-4}$alkylthio such as methylthio or ethylthio groups.

In the compounds of formula (1), derivatives of the carboxylic acid group R include carboxylic acid esters and amides. Particular esters and amides include —CO$_2$Alk$^1$ and —CONR$^5$R$^6$ groups as described herein.

When Alk$^a$ is present in compounds of formula (1) as an optionally substituted aliphatic or heteroaliphatic chain it may be for example any divalent chain corresponding to the below-mentioned aliphatic or heteroaliphatic groups described for R$^3$.

Aromatic groups represented by the group Ar$^1$ in compounds of the invention include for example monocyclic or bicyclic fused ring $C_{6-12}$ aromatic groups, such as phenyl, 1- or 2-naphthyl, 1- or 2-tetrahydronaphthyl, indanyl or indenyl groups.

Heteroaromatic groups represented by the group Ar$^1$ in the compounds of formula (1) include for example $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N—$C_{1-6}$-alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, benzothienyl, benzotriazolyl, indolyl, indolinyl, isoindolyl, indazolinyl, benzimidazolyl, imidazo[1,2-a]pyridyl, benzothiazolyl, benzoxazolyl, benzisoxazolyl, benzopyranyl, [3,4-dihydro]benzopyranyl, quinazolinyl, quinoxalinyl, naphthyridinyl, pyrido[3,4-b]pyridyl, pyrido [3,2-b]pyridyl, pyrido[4,3-b]-pyridyl, quinolinyl, isoquinolinyl, tetrazolyl, 5,6,7,8-tetrahydroquinolinyl, 5,6,7, 8-tetrahydroisoquinolinyl, and imidyl, e.g. succinimidyl, phthalimidyl, or naphthalimidyl such as 1,8-naphthalimidyl.

Each aromatic or heteroaromatic group represented by the group Ar$^1$ may be optionally substituted on any available carbon or, when present, nitrogen atom. One, two, three or more of the same or different substituents may be present and each substituent may be selected for example from an atom or group -L$^2$(Alk)$_t$L$^3$(R$^4$)$_u$ in which L$^2$ and L$^3$, which may be the same or different, is each a covalent bond or a linker atom or group, t is zero or the integer 1, u is an integer 1, 2 or 3, Alk is an aliphatic or heteroaliphatic chain and R$^4$ is a hydrogen or halogen atom or a group selected from $C_{1-6}$alkyl, —OR$^5$ [where R$^5$ is a hydrogen atom or an optionally substituted $C_{1-6}$alkyl group], —SR$^5$, —NR$^5$R$^6$ [where R$^6$ is as just defined for R$^5$ and may be the same or different], —NO$_2$, —CN, —CO$_2$R$^5$, —SO$_3$H, —SO$_3$R$^5$, —SOR$^5$, —SO$_2$R$^5$, —OCO$_2$R$^5$, —CONR$^5$R$^6$, —OCONR$^5$R$^6$, —CSNR$^5$R$^6$, —COR$^5$, —OCOR$^5$, —N(R$^5$) COR$^6$, —N(R$^5$)CSR$^6$, —SO$_2$N(R$^5$)(R$^6$), —N(R$^5$)SO$_2$R$^6$, N(R$^5$)CON(R$^6$)(R$^7$) [where R$^7$ is a hydrogen atom or an optionally substituted $C_{1-6}$alkyl group], —N(R$^5$)CSN(R$^6$) (R$^7$) or —N(R$^5$)SO$_2$N(R$^6$)(R$^7$), provided that when t is zero and each of L$^2$ and L$^3$ is a covalent bond then u is the integer 1 and R$^4$ is other than a hydrogen atom When L$^2$ and/or L$^3$ is present in these substituents as a linker atom or group it may be any divalent linking atom or group. Particular examples include —O— or —S— atoms or —C(O)—, —C(O)O—, —OC(O)—, —C(S)—, —S(O)—, —S(O)$_2$—, —N(R$^8$)— [where R$^8$ is a hydrogen atom or an optionally substituted $C_{1-6}$alkyl group], —CON (R$^8$)—, —OC(O)N(R$^8$)—, —CSN(R$^8$)—, —N(R$^8$)CO—, —N(R$^8$)C(O)O—, —N(R$^8$)CS—, —S(O)$_2$N(R$^8$)—, —N(R$^8$)S(O)$_2$—, —N(R$^8$)CON(R$^8$)—, —N(R$^8$)CSN(R$^8$)—, or —N(R$^8$)SO$_2$N(R$^8$)— groups. Where the linker group contains two R$^8$ substituents, these may be the same or different.

When R$^c$, R$^d$, R$^e$, R$^f$, R$^4$, R$^5$, R$^6$, R$^7$ and/or R$^8$ is present as a C$_{1-6}$alkyl group it may be a straight or branched C$_{1-6}$alkyl group, e.g. a C$_{1-3}$alkyl group such as a methyl or ethyl group. Optional substituents which may be present on such groups include for example one, two or three substituents which may be the same or different selected from halogen atoms, for example fluorine, chlorine, bromine or iodine atoms, or hydroxy or C$_{1-6}$alkoxy e.g. methoxy or ethoxy groups.

When Alk is present as an aliphatic or heteroaliphatic chain it may be for example any divalent chain corresponding to the below-mentioned aliphatic or heteroaliphatic group described for R$^3$.

Halogen atoms represented by R$^4$ in the optional Ar$^1$ substituents include fluorine, chlorine, bromine, or iodine atoms.

Examples of the substituents represented by -L$^2$(Alk)$_t$L$^3$(R$^4$)$_u$ when present in Ar$^1$ groups in compounds of the invention include atoms or groups -L$^2$AlkL$^3$R$^4$, -L$^2$AlkR$^4$, -L$^2$R$^4$ and -AlkR$^4$ wherein L$^2$, Alk, L$^3$ and R$^4$ are as defined above. Particular examples of such substituents include -L$^2$CH$_2$L$^3$R$^4$, -L$^2$CH(CH$_3$)L$^3$R$^4$, -L$^2$CH$_2$(CH$_2$)$_2$L$^3$R$^4$, -L$^2$CH$_2$R$^4$, -L$^2$CH(CH$_3$)R$^4$, -L$^2$(CH$_2$)$_2$R$^4$, —CH$_2$R$^4$, —CH(CH$_3$)R$^4$, —CH$_2$)$_2$R$^4$ and —R$^4$ groups.

Thus Ar$^1$ in compounds of the invention may be optionally substituted for example by one, two, three or more halogen atoms, e.g. fluorine, chlorine, bromine or iodine atoms, and/or C$_{1-6}$alkyl, e.g. methyl, ethyl, n-propyl, i-propyl, n-butyl or t-butyl, C$_{1-6}$alkylamino, e.g. methylamino or ethylamino, C$_{1-6}$hydroxyalkyl, e.g. hydroxymethyl, hydroxyethyl or —C(OH)(CF$_3$)$_2$, carboxyC$_{1-6}$alkyl, e.g. carboxyethyl, C$_{1-6}$alkylthio e.g. methylthio or ethylthio, carboxyC$_{1-6}$alkylthio, e.g. carboxymethylthio, 2-carboxyethylthio or 3-carboxypropylthio, C$_{1-6}$alkoxy, e.g. methoxy or ethoxy, optionally substituted C$_{6-12}$arylC$_{1-6}$alkyloxy e.g. benzyloxy, hydroxyC$_{1-6}$alkoxy, e.g. 2-hydroxyethoxy, haloC$_{1-6}$alkyl, e.g. —CF$_3$, —CHF$_2$, CH$_2$F, haloC$_{1-6}$alkoxy, e.g. —OCF$_3$, —OCHF$_2$, —OCH$_2$F, C$_{1-6}$alkylamino, e.g. methylamino or ethylamino, amino (—NH$_2$), aminoC$_{1-6}$alkyl, e.g. aminomethyl or aminoethyl, C$_{1-6}$dialkylamino, e.g. dimethylamino or diethylamino, C$_{1-6}$alkylaminoC$_{1-6}$alkyl, e.g. ethylaminoethyl, C$_{1-6}$ dialkylaminoC$_{1-6}$alkyl, e.g. diethylaminoethyl, aminoC$_{1-6}$alkoxy, e.g. aminoethoxy, hydroxyC$_{1-6}$alkylamino e.g. hydroxyethylamino or hydroxypropylamino, C$_{1-6}$alkylaminoC$_{1-6}$alkoxy, e.g. methylaminoethoxy, C$_{1-6}$dialkylaminoC$_{1-6}$alkoxy, e.g. dimethylaminoethoxy, diethylaminoethoxy, diisopropylaminoethoxy, or dimethylaminopropoxy, nitro, cyano, amidino, hydroxyl (—OH), formyl [HC(O)—], carboxyl (—CO$_2$H), —CO$_2$Alk$^1$ [where Alk$^1$ is as defined below], C$_{1-6}$ alkanoyl e.g. acetyl, thiol (—SH), thioC$_{1-6}$alkyl, e.g. thiomethyl or thioethyl, thioC$_{1-6}$alkylC$_{6-12}$aryl e.g. thiobenzyl, sulphonyl (—SO$_3$H), —SO$_3$Alk$^1$, C$_{1-6}$alkylsulphinyl e.g. methylsulphinyl or ethylsulphinyl, C$_{1-6}$alkylsulphonyl, e.g. methylsulphonyl, aminosulphonyl (—SO$_2$NH$_2$), C$_{1-6}$alkylaminosulphonyl, e.g. methylaminosulphonyl or ethylaminosulphonyl, C$_{1-6}$dialkylaminosulphonyl, e.g. dimethylaminosulphonyl or diethylaminosulphonyl, optionally substituted phenylaminosulphonyl, carboxamido (—CONH$_2$), C$_{1-6}$alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, aminoC$_{1-6}$alkylaminocarbonyl, e.g. aminoethylaminocarbonyl, C$_{1-6}$dialkylaminoC$_{1-6}$alkylaminocarbonyl, e.g. diethylaminoethylaminocarbonyl, aminocarbonylamino, C$_{1-6}$alkylaminocarbonylamino, e.g. methylaminocarbonylamino or ethylaminocarbonylamino, C$_{1-6}$dialkylaminocarbonylamino, e.g. dimethylaminocarbonylamino or diethylaminocarbonylamino, C$_{1-6}$alkylaminocabonylC$_{1-6}$alkylamino, e.g. methylaminocarbonylmethylamino, aminothiocarbonylamino, C$_{1-6}$alkylaminothiocarbonylamino, e.g. methylaminothiocarbonylamino or ethylaminothiocarbonylamino, C$_{1-6}$dialkylaminothiocarbonylamino, e.g. dimethylaminothiocarbonylamino or diethylaminothiocarbonylamino, C$_{1-6}$alkylaminothiocarbonylC$_{1-6}$alkylamino, e.g. ethylaminothiocarbonylmethylamino, C$_{1-6}$alkylsulphonylamino, e.g. methylsulphonylamino or ethylsulphonylamino, C$_{1-6}$dialkylsulphonylamino, e.g. dimethylsulphonylamino or diethylsulphonylamino, aminosulphonylamino (—NHSO$_2$NH$_2$), C$_{1-6}$alkylamino-sulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, C$_{1-6}$alkanoylamino, e.g. acetylamino, aminoC$_{1-6}$alkanoylamino e.g. aminoacetylamino, C$_{1-6}$dialkylaminoC$_{1-6}$alkanoylamino, e.g. dimethylaminoacetylamino, C$_{1-6}$alkanoylaminoC$_{1-6}$alkyl, e.g. acetylaminomethyl, C$_{1-6}$alkanoylaminoC$_{1-6}$alkylamino, e.g. acetamidoethylamino, C$_{1-6}$alkoxycarbonylamino, e.g. methoxycarbonylamino, ethoxycarbonylamino or t-butoxycarbonylamino groups.

When the group R$^3$ is present in compounds of formula (1) as an optionally substituted aliphatic group it may be an optionally substituted C$_{1-10}$ aliphatic group. Particular examples include optionally substituted straight or branched chain C$_{1-6}$ alkyl, C$_{2-6}$ alkenyl, or C$_{2-6}$ alkynyl groups.

Heteroaliphatic groups represented by the group R$^3$ include the aliphatic groups just described but with each group additionally containing one, two, three or four heteroatoms or heteroatom-containing groups. Particular heteroatoms or groups include atoms or groups L$^4$ where L$^4$ is as defined above for L$^2$ when L$^2$ is a linker atom or group. Each L$^4$ atom or group may interrupt the aliphatic group, or may be positioned at its terminal carbon atom to connect the group to an adjoining atom or group.

Particular examples of aliphatic groups represented by the group R$^3$ include optionally substituted —CH$_3$, —CH$_2$CH$_3$, —CH(CH$_3$)$_2$, —(CH$_2$)$_2$CH$_3$, —CH(CH$_3$)CH$_3$, —CH$_2$)$_3$CH$_3$, —CH(CH$_3$)CH$_2$CH$_3$, —CH$_2$CH(CH$_3$)$_2$, —C(CH$_3$)$_3$, —(CH$_2$)$_4$CH$_3$, —(CH$_2$)$_5$CH$_3$, —CHCH$_2$, —CHCHCH$_3$, —CH$_2$CHCH$_2$, —CHCHCH$_2$CH$_3$, —CH$_2$CHCHCH$_3$, —(CH$_2$)$_2$CHCH$_2$, —CCH, —CCCH$_3$, —CH$_2$CCH, —CCCH$_2$CH$_3$, —CH$_2$CCCH$_3$, or —(CH$_2$)$_2$CCH groups. Where appropriate each of said groups may be optionally interrupted by one or two atoms and/or groups L$^4$ to form an optionally substituted heteroaliphatic group. Particular examples include optionally substituted -L$^4$CH$_3$, —CH$_2$L$^4$CH$_3$, -L$^4$CH$_2$CH$_3$, —CH$_2$L$^4$CH$_2$CH$_3$, —(CH$_2$)$_2$L$^4$CH$_3$, -L$^4$(CH$_2$)$_3$CH$_3$ and —(CH$_2$)$_2$L$^4$CH$_2$CH$_3$ groups.

The optional substituents which may be present on aliphatic or heteroaliphatic chains represented by R$^3$ include one, two, three or more substituents where each substituent may be the same or different and is selected from halogen atoms, e.g. fluorine, chlorine, bromine or iodine atoms, or hydroxy, $C_{1-6}$alkoxy, e.g. methoxy or ethoxy, thiol, $C_{1-6}$alkylthio e.g. methylthio or ethylthio, amino or substituted amino groups. Substituted amino groups include —NHR$^9$ and —N(R$^9$)$_2$ groups where R$^9$ is an optionally substituted straight or branched $C_{1-6}$alkyl group as defined above for R$^4$. Where two R$^9$ groups are present these may be the same or different. Particular examples of substituted groups represented by R$^3$ include those specific groups just described substituted by one, two, or three halogen atoms such as fluorine atoms, for example groups of the type —CHCF$_3$, —CH(CF$_3$)$_2$, —CH$_2$CH$_2$CF$_3$, —CH$_2$CH(CF$_3$)$_2$ and —C(CF$_3$)$_2$CH$_3$.

Optionally substituted cycloaliphatic groups represented by the group R$^3$ in compounds of the invention include optionally substituted $C_{3-10}$ cycloaliphatic groups. Particular examples include optionally substituted $C_{3-10}$ cycloalkyl, e.g. $C_{3-7}$ cycloalkyl or $C_{3-10}$ cycloalkenyl, e.g $C_{3-7}$ cycloalkenyl groups.

Optionally substituted heterocycloaliphatic groups represented by the group R$^3$ include optionally substituted $C_{3-10}$heterocycloaliphatic groups. Particular examples include optionally substituted $C_{3-10}$heterocycloalkyl, e.g. $C_{3-7}$ heterocycloalkyl, or $C_{3-10}$heterocycloalkenyl, e.g. $C_{3-7}$ hetercycloalkenyl groups, each of said groups containing one, two, three or four heteroatoms or heteroatom-containing groups L$^4$ as defined above.

Optionally substituted polycycloaliphatic groups represented by the group R$^3$ include optionally substituted $C_{7-10}$ bi- or tricycloalkyl or $C_{7-10}$bi- or tricycloalkenyl groups. Optionally substituted heteropolycycloaliphatic groups represented by the group R$^3$ include the optionally substituted polycycloalkyl groups just described, but with each group additionally containing one, two, three or four L$^4$ atoms or groups.

Particular examples of cycloaliphatic, polycycloaliphatic, heterocycloaliphatic and heteropolycycloaliphatic groups represented by the group R$^3$ include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, tetrahydrofuranyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, thiazolinyl, thiazolidinyl, pyranyl, e.g. 2- or 4-pyranyl, piperidinyl, piperidinone, 1,4-dioxanyl, morpholinyl, morpholinone, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,-oxadiazinyl groups.

The optional substituents which may be present on the cycloaliphatic, polycycloaliphatic, heterocycloaliphatic or heteropolycycloaliphatic groups represented by the group R$^3$ include one, two, three or more substituents each selected from halogen atoms, e.g. fluorine, chlorine, bromine or iodine atoms, or $C_{1-6}$alkyl, e.g. methyl or ethyl, halo$C_{1-6}$ alkyl, e.g. halomethyl or haloethyl such as difluoromethyl or trifluoromethyl, optionally substituted by hydroxyl, e.g. —C(OH)(CF$_3$)$_2$, hydroxyl, $C_{1-6}$alkoxy, e.g. methoxy or ethoxy, halo$C_{1-6}$alkoxy, e.g. halomethoxy or haloethoxy such as difluoromethoxy or trifluoromethoxy, thiol, $C_{1-6}$alkylthio e.g. methylthio or ethylthio, or -(Alk$^2$)$_v$R$^{10}$ groups in which Alk$^2$ is a straight or branched $C_{1-3}$ alkylene chain, v is zero or an integer 1 and R$^{10}$ is a —OH, —SH, —N(R$^{11}$)$_2$, —CN, —CO$_2$R$^{11}$, —NO$_2$, —CON(R$^{11}$)$_2$, CSN (R$^{11}$)$_2$, —OC(O)N(R$^{11}$)$_2$, —C(O)H, —COR$^{11}$, —OCO$_2$R$^{11}$, —OC(O)R$^{11}$, —C(S)R$^{11}$, —CSN(R$^{11}$)$_2$, —N(R$^{11}$)COR$^{11}$, —N(R$^{11}$)CSR$^{11}$, —SO$_3$H, —SOR$^{11}$, —SO$_2$R$^{11}$, —SO$_3$R$^{11}$, —SO$_2$N(R$^{11}$)$_2$, —N(R$^{11}$)SO$_2$R$^{11}$, —N(R$^{11}$)CON(R$^{11}$)$_2$, —N(R$^{11}$)CSN(R$^{11}$)$_2$ or —N(R$^{11}$)SO$_2$N(R$^{11}$)$_2$ [in which R$^{11}$ is an atom or group as defined herein for R$^8$ or an optionally substituted cycloaliphatic or heterocycloaliphatic group as previously defined for R$^3$] aromatic or heteroaromatic group. Where two R$^{11}$ atoms or groups are present in these substituents these may be the same or different.

Additionally, when the group R$^3$ is a heterocycloaliphatic group containing one or more nitrogen atoms each nitrogen atom may be optionally substituted by a group -(L$^5$)$_p$(Alk$^3$)$_q$R$^{12}$ in which L$^5$ is —C(O)—, —C(O)O—, —C(S)—, —S(O)—, —S(O)$_2$—, —CON(R$^{11}$)—, —CSN(R$^{11}$)—, —SON(R$^{11}$)— or SO$_2$N(R$^{11}$)—; p is zero or an integer 1; Alk$^3$ is an optionally substituted aliphatic or heteroaliphatic chain; q is zero or an integer 1; and R$^{12}$ is a hydrogen atom or an optionally substituted cycloaliphatic, heterocycloaliphatic, polycycloaliphatic, polyheterocycloaliphatic, aromatic or heteroaromatic group.

Optionally substituted aliphatic or heteroaliphatic chains represented by Alk$^3$ include those optionally substituted chains described above for R$^3$. Cycloaliphatic, heterocycloaliphatic, polycyloaliphatic or polyheterocycloaliphatic groups represented by R$^{12}$ include those groups just described for the group R$^3$. Optional substituents which may be present on these groups include those described above in relation to R$^3$ aliphatic and heteroaliphatic chains.

Optionally substituted aromatic and heteroaromatic groups represented by the group R$^3$ in compounds of the invention include those groups as described above in relation to Ar$^1$. The aromatic or heteroaromatic group may be attached to the remainder of the compound of formula (1) by any appropriate carbon on hetero e.g. nitrogen atom.

Optional substituents which may be present on the aromatic or heteroaromatic groups represented by the group R$^3$ include one, two, three or more substituents, each selected from an atom or group R$^{13}$ in which R$^{13}$ is —R$^{13a}$ or -Alk$^4$(R$^{13a}$)$_m$, where R$^{13a}$ is a halogen atom, or an amino (—NH$_2$), substituted amino, nitro, cyano, amidino, hydroxyl (—OH), substituted hydroxyl, formyl, carboxyl (—CO$_2$H), esterified carboxyl, thiol (—SH), substituted thiol, —COR$^{14}$ [where R$^{14}$ is an -Alk$^4$(R$^{13a}$)$_m$, aryl or heteroaryl group], —CSR$^{14}$, —SO$_3$H, —SOR$^{14}$, —SO$_2$R$^{14}$, —SO$_2$NH$_2$, —SO$_2$NHR$^{14}$SO$_2$N(R$^{14}$)$_2$, —CONH$_2$, —CSNH$_2$, —CONHR$^{14}$, —CSNHR$^{14}$, —CON[R$^{14}$]$_2$, —CSN(R$^{14}$)$_2$, —N(R$^{11}$)SO$_2$R$^{14}$, —N(SO$_2$R$^{14}$)$_2$, —N(R$^{11}$)SO$_2$NH$_2$, —N(R$^{11}$)SO$_2$NHR$^{14}$, —N(R$^{11}$)SO$_2$N(R$^{14}$)$_2$, —N(R$^{11}$) COR$^{14}$, —N(R$^{11}$)CONH$_2$, —N(R$^{11}$)CONHR$^{14}$, —N(R$^{11}$) CON(R$^{14}$)$_2$, —N(R$^{11}$)CSNH$_2$, —N(R$^{11}$)CSNHR$^{14}$, —N(R$^{11}$)CSN(R$^{14}$)$_2$, —N(R$^{11}$)CSR$^{14}$, —N(R$^{11}$)C(O)OR$^{14}$, —SO$_2$NHet$^1$ [where —NHet$^1$ is an optionally substituted $C_{5-7}$cyclicamino group optionally containing one or more other —O— or —S— atoms or —N(R$^{11}$)—, —C(O)— or —C(S)— groups], —CONHet$^1$, —CSNHet$^1$, —N(R$^{11}$) SO$_2$NHet$^1$, —N(R$^{11}$)CONHet$^1$, —N(R$^{11}$)CSNHet$^1$, —SO$_2$N(R$^{11}$)Het$^2$ [where Het$^2$ is an optionally substituted monocyclic $C_{5-7}$carbocyclic group optionally containing one or more —O— or —S— atoms or —N(R$^{11}$)—, —C(O)— or —C(S)— groups), -Het$_2$, —CON(R$^{11}$)Het$^2$, —CSN(R$^{11}$)Het$^2$, —N(R$^{11}$)CON(R$^{11}$)Het$^2$, —N(R$^{11}$)CSN (R$^{11}$)Het$^2$, aryl or heteroaryl group; Alk$^4$ is a straight or branched $C_{1-6}$alkylene, $C_{2-6}$alkenylene or $C_{2-6}$alkynylene chain, optionally interrupted by one, two or three —O— or —S— atoms or —S(O)$_n$ [where n is an integer 1 or 2] or —N(R$^{15}$)— groups [where R$^{15}$ is a hydrogen atom or $C_{1-6}$alkyl, e.g. methyl or ethyl group]; and m is zero or an integer 1, 2 or 3. It will be appreciated that when two $R^{11}$ or $R^{14}$ groups are present in one of the above substituents, the $R^{11}$ or $R^{14}$ groups may be the same or different.

When in the group -Alk$^4$($R^{13a}$)$_m$ m is an integer 1, 2 or 3, it is to be understood that the substituent or substituents $R^{13a}$ may be present on any suitable carbon atom in -Alk$^4$. Where more than one $R^{13a}$ substituent is present these may be the same or different and may be present on the same or different atom in -Alk$^4$. Clearly, when m is zero and no substituent $R^{13a}$ is present the alkylene, alkenylene or alkynylene chain represented by Alk$^4$ becomes an alkyl, alkenyl or alkynyl group.

When $R^{13a}$ is a substituted amino group it may be for example a group —NHR$^{14}$ [where $R^{14}$ is as defined above) or a group —N($R^{14}$)$_2$ wherein each $R^{14}$ group is the same or different.

When $R^{13a}$ is a halogen atom it may be for example a fluorine, chlorine, bromine, or iodine atom.

When $R^{13a}$ is a substituted hydroxyl or substituted thiol group it may be for example a group —OR$^{14}$ or a —SR$^{14}$ or —SC(=NH)NH$_2$ group respectively.

Esterified carboxyl groups represented by the group $R^{13a}$ include groups of formula —CO$_2$Alk$^1$ wherein Alk$^1$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the Alk$^1$ group include $R^{13a}$ substituents described above.

When Alk$^4$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N($R^{12}$)— groups.

Aryl or heteroaryl groups represented by the groups $R^{13a}$ or $R^{14}$ include mono- or bicyclic optionally substituted $C_{6-12}$ aromatic or $C_{1-9}$ heteroaromatic groups as described above for the group Ar$^1$. The aromatic and heteroaromatic groups may be attached to the remainder of the compound of formula (1) by any carbon or hetero e.g. nitrogen atom as appropriate.

When —NHet$^1$ or -Het$^2$ forms part of a substituent $R^{13}$ each may be for example an optionally substituted pyrrolidinyl, pyrazolidinyl, piperazinyl, morpholinyl, thiomorpholinyl, piperidinyl or thiazolidinyl group. Additionally Het$^2$ may represent for example, an optionally substituted cyclopentyl or cyclohexyl group. Optional substituents which may be present on —NHet$^1$ or -Het$^2$ include those substituents as described for $R^3$ cycloaliphatic groups above.

Particularly useful atoms or groups represented by $R^{13}$ include fluorine, chlorine, bromine or iodine atoms, or $C_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, thienyl, morpholinyl, thiomorpholinyl, piperazinyl, pyrrolidinyl, or piperidinyl, $C_{1-6}$alkylamino, e.g. methylamino or ethylamino, $C_{1-6}$hydroxyalkyl, e.g. hydroxymethyl or hydroxyethyl, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, optionally substituted phenoxy, pyridyloxy, thiazolyoxy, phenylthio e.g. 3,5-dimethoxyphenylthio, or pyridylthio, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$alkylamino, e.g. methylamino, ethylamino or propylamino, optionally substituted $C_{6-12}$aryl$C_{1-6}$alkylamino e.g. benzylamino, amino (—NH$_2$), amino$C_{1-6}$alkyl, e.g. aminomethyl or aminoethyl, $C_{1-6}$dialkylamino, e.g. dimethylamino or diethylamino, amino$C_{1-6}$alkylamino e.g. aminomethylamino, aminoethylamino or aminopropylamino, optionally substituted Het$^1$N$C_{1-6}$alkylamino e.g. morpholinopropylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, diisopropylaminoethoxy, or dimethylaminopropoxy, hydroxy$C_{1-6}$alkylamino, e.g. hydroxyethylamino or hydroxypropylamino, imido, such as phthalimido or naphthalimido, e.g. 1,8-naphthalimido, nitro, cyano, amidino, hydroxyl (—OH), formyl [HC(O)—], carboxyl (—CO$_2$H), —CO$_2$Alk$^5$ [where Alk$^5$ is as defined above], $C_{1-6}$ alkanoyl e.g. acetyl, optionally substituted benzoyl, thiol (—SH), thio$C_{1-6}$alkyl, e.g. thiomethyl or thioethyl, —SC(=NH)NH$_2$, sulphonyl (—SO$_3$H), $C_{1-6}$alkylsulphinyl, e.g. methylsulphinyl, ethylsulphinyl or propylsulphinyl, $C_{1-6}$alkylsulphonyl, e.g. methylsulphonyl, ethylsulphonyl or propylsulphonyl, optionally substituted $C_{6-10}$arylsulphonyl e.g. phenylsulphonyl, dichlorophenylsulphonyl, aminosulphonyl (—SO$_2$NH$_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, optionally substituted phenylaminosulphonyl, carboxamido (—CONH$_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocarbonyl$C_{1-6}$alkylamino, e.g. methylaminocarbonylmethylamino, aminothiocarbonylamino, $C_{1-6}$alkyl-aminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkyl-amino, e.g. ethylaminothiocarbonylmethylamino, —CONHC(=NH)NH$_2$, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, optionally substituted phenylsulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, optionally substituted morpholinesulphonylamino or morpholinesulphonyl$C_{1-6}$alkyl-amino, optionally substituted phenylaminosulphonylamino, $C_{1-6}$alkanoyl-amino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$ alkyl, e.g. acetylaminomethyl, $C_{1-6}$alkanoylamino$C_{1-6}$ alkylamino, e.g. acetamidoethylamino, $C_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylamino$C_{1-6}$alkyl e.g. benzyloxycarbonylaminoethyl, thiobenzyl, pyridylmethylthio or thiazolylmethylthio groups.

Where desired, two $R^{13}$ substituents may be linked together to form a cyclic group such as a cyclic ether, e.g. a $C_{1-6}$alkylenedioxy group such as methylenedioxy or ethylenedioxy.

It will be appreciated that where two or more $R^{13}$ substituents are present, these need not necessarily be the same atoms and/or groups. In general, the substituent(s) may be present at any available ring position in the aromatic or heteroaromatic group represented by $R^3$.

Nitrogen-containing six-membered heteroarylene groups represented by the group $Ar^2$ in compounds of formula (1) include pyridiyl, pyrimidindiyl, pyridazindiyl, pyrazindiyl and triazindiyl groups. Each group may be attached to the remainder of the molecule through any available ring carbon atom.

The phenylene and nitrogen-containing heteroarylene groups represented by $Ar^2$ may be optionally substituted by one or two substituents selected from the atoms or groups -$L^2(Alk)_tL^3(R^4)_u$ described herein. Where two of these atoms or groups are present they may be the same or different.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or en isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In the compounds according to the invention the group $Ar^1$ is preferably an optionally substituted phenyl or monocyclic heteroaromatic group. Particularly useful groups of this type are optionally substituted five- or six-membered heteroaromatic groups as described previously, especially five- or six-membered heteroaromatic groups containing one or two heteroatoms selected from oxygen, sulphur or nitrogen atoms. Nitrogen-containing groups are especially useful, particularly pyridyl or pyrimidinyl groups. Particularly useful substituents present on $Ar^1$ groups include halogen atoms or alkyl, —$OR^5$, —$SR^5$, —$NR^5R^6$, —$CO_2H$, —$CO_2CH_3$, $NO_2$ or —CN groups as described above in relation to the compounds of formula (1).

In one group of compounds of formula (1) for example $R^a$ and $R^{a'}$ is each a hydrogen atom, r is zero and R is a carboxylic acid (—$CO_2H$).

A particularly useful group of compounds according to the invention has the formula (2):

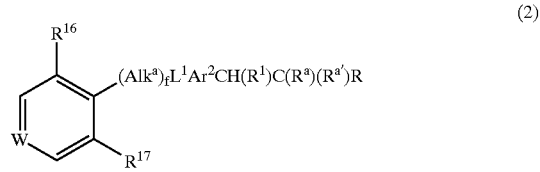

(2)

wherein —W═ is —CH═ or —N═;
$R^{16}$ and $R^{17}$, which may be the same or different is each a hydrogen atom or an atom or group -$L^2(Alk)_tL^3(R^4)_u$ in which $L^2$, Alk, t, $L^3$, $R^4$ and u are as defined previously; $Alk^a$, $L^1$, $R^1$, $Ar^2$, $R^a$ and R are as defined for formula (1); and the salts, solvates, hydrates and N-oxides thereof.

—W═ in compounds of formula (2) is preferably —N═.
$R^{16}$ and $R^{17}$ in compounds of formula (2) is each preferably as particularly described above for compounds of formula (1), other than a hydrogen atom. Particularly useful $R^{16}$ and $R^{17}$ substituents include halogen atoms, especially fluorine or chlorine atoms, or methyl, halomethyl, especially —$CF_3$, —$CHF_2$ or —$CH_2F$, methoxy or halomethoxy, especially —$OCF_3$, —$OCHF_2$ or —$OCH_2F$ groups. Especially prefered $R^{16}$ and $R^{17}$ substituents are chlorine atoms.

R in the compounds of formulae (1) and (2) is preferably a —$CO_2H$ group.

In one preferred group of compounds of formulae (1) and (2) r is preferably zero and $L^1$ is preferably —$CON(R^2)$—. An especially useful $L^1$ group is —CONH—.

In another preferred group of compounds of formulae (1) and (2) r is preferably the integer 1 and $Alk^a$ is preferably an aliphatic chain, particularly a $C_{1-6}$alkyl chain, most especially a —$CH_2$— group. In this group of compounds $L^1$ is preferably an —O— atom.

$R^a$ in compounds of formulae (1) and (2) is preferably a hydrogen atom or an —OH group. An especially preferred $R^a$ atom in compounds of formula (1) and (2) is a hydrogen atom.

The group $Ar^2$ in compounds of formulae (1) and (2) is preferably an optionally substituted phenylene group. Particularly useful groups include optionally substituted 1,4-phenylene groups.

Particularly useful $R^1$ groups in compounds of the invention are those wherein $R^1$ is a —$NHCOR^3$ or —$NHR^3$ group.

In general in compounds of formulae (1) and (2) the group $R^3$ may especially be an optionally substituted cycloaliphatic, heterocycloaliphatic, aromatic or heteroaromatic group as defined herein. Particularly useful groups of this type include optionally substituted $C_{5-7}$cycloaliphatic, especially optionally substituted cyclopentyl and cyclohexyl, optionally substituted $C_{5-7}$heterocycloaliphatic, especially optionally substituted pyrrolidinyl or thiazolidinyl, optionally substituted phenyl and optionally substituted $C_{5-7}$heteroaromatic, especially optionally substituted pyridyl and 1,3,5-triazinyl groups.

Optional substituents on these groups include in particular $R^{13}$ atoms or groups where $R^3$ is an aromatic or heteroaromatic group. Particularly useful $R^{13}$ atoms or groups include a halogen atom, especially fluorine or chlorine, $C_{1-6}$alkoxy, especially methoxy, optionally substituted phenoxy and phenylthio, especially phenoxy and 2,5-dimethoxyphenylthio, hydroxy$C_{1-6}$alkylamino, especially hydroxyethylamino, $C_{1-6}$alkylsulphinyl especially propylsulphinyl, $C_{1-6}$alkylsulphonyl, especially propylsulphonyl or $C_{6-10}$arylsulphonyl, especially phenylsulphonyl or dichlorophenylsulphonyl.

Where $R^3$ is a nitrogen-containing heterocycloaliphatic group such as a pyrrolidinyl or thiazolidinyl group optional substituents include in particular $-(L^5)_p(Alk^3)_qR^{12}$ groups as described earlier.

Particularly useful $-(L^5)_p(Alk^3)_qR^{12}$ groups include those in which p is the integer 1 and $L^5$ is a —CO— or —S(O)$_2$— group. When $L^5$ is —CO— $Alk^3$ is preferably present (i.e. q is preferably an integer 1) and in particular is a —CH$_2$- chain. $R^{12}$ in groups of this type is preferably a hydrogen atom. When $L^5$ is —S(O)$_2$— q is preferably zero. Compounds of this type in which $R^{12}$ is an optionally substituted aromatic or heteroaromatic group, especially an optionally substituted phenyl, e.g. dichlorophenyl, pyridyl or imidazolyl group are particularly preferred.

Particularly useful compounds of the invention include:

3-{4-[(3,5-Dichloroisonicotinoyl)amino]phenyl}-3-({4-[2-hydroxyethylamino]-6-methoxy-1,3,5-triazin-2-yl}amine)propanoic acid;

3-[(3,5-Dichloroisonicotinoyl)amino]-3-{4-[(3,5-dichloroisonicotinoyl)amino]phenyl}propanoic acid;

3-{4-[(3,5-Dichloroisonicotinoyl)amino]phenyl}-3-[(2,6-dimethoxybenzoyl)amino]propanoic acid;

3-({[(4S)-3-Acetyl-1,3-thiazolinan-4-yl]carbonyl}amino-3-{4-[(3,5-dichloroisonicotinoyl)amino]phenyl}propanoic acid;

3-{4-[(3,5-Dichloroisonicotinoyl)amino]phenyl}-3-[({(2S)-1-[(3,5-dichlorophenyl)sulphonyl]tetrahydro-1-H-pyrrol-2-yl}carbonyl)amino]propanoic acid;

(2RS,3RS)-3-{4-[(3,5-Dichloroisonicotinoyl)amino]phenyl}-3-{[((2S)-1-[(3,5-dichlorophenyl)sulphonyl]tetrahydro-1-H-pyrrol-2-yl)carbonyl]amino}-2-hydroxypropanoic acid;

3-{4-[(3,5-Dichloroisonicotinoyl)amino]phenyl}-3-[({2-[(2,5-dimethoxyphenyl)thio]-3-pyridinyl}carbonyl)amino]propanoic acid;

and the salts, solvates, hydrates and N-oxides thereof.

Compounds according to the invention are potent and selective inhibitors of α4 integrins. The ability of the compounds to act in this way may be simply determined by employing tests such as those described in the Examples hereinafter.

The compounds are of use in modulating cell adhesion and in particular are of use in the prophylaxis and treatment of diseases or disorders involving inflammation in which the extravasation of leukocytes plays a role and the invention extends to such a use and to the use of the compounds for the manufacture of a medicament for treating such diseases or disorders.

Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $Ar^1$, $Alk^a$, $L^1$, $Ar^2$, $R^1$, $R^a$, $R^{a'}$ and R when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formula (2).

Thus according to a further aspect of the invention, a compound of formula (1) in which R is a —$CO_2H$ group may be obtained by hydrolysis of an ester of formula (3):

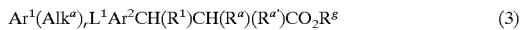

$$Ar^1(Alk^a)_rL^1Ar^2CH(R^1)CH(R^a)(R^{a'})CO_2R^g \quad (3)$$

where $R^g$ is an alkyl group, for example a $C_{1-6}$alkyl group as described above.

The hydrolysis may be performed using either an acid or a base depending on the nature of $R^g$, for example an organic acid such as trifluoroacetic acid or an inorganic base such as lithium or potassium hydroxide optionally in an aqueous organic solvent such as an amide, e.g. a substituted amide such as dimethylformamide, an ether, e.g. a cyclic ether such as tetrahydrofuran or dioxane or an alcohol, e.g. methanol at around ambient temperature. Where desired, mixtures of such solvents may be used.

Esters of formula (3) in which $R^1$ is a —$NHCOR^3$ group may be prepared by coupling an amine of formula (4):

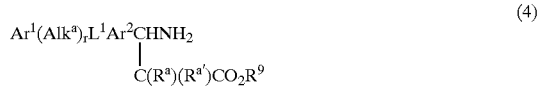

$$Ar^1(Alk^a)_rL^1Ar^2CHNH_2 \\ | \\ C(R^a)(R^{a'})CO_2R^9 \quad (4)$$

or a salt thereof with an acid $R^3CO_2H$ or an active derivative thereof. Active derivatives of acids include anhydrides, esters and halides.

The coupling reaction may be performed using standard conditions for reactions of this type. Thus for example the reaction may be carried out in a solvent, for example an inert organic solvent such as an amide, e.g. a substituted amide such as dimethylformamide, an ether, e.g. a cyclic ether such as tetrahydrofuran, or a halogenated hydrocarbon, such as dichloromethane, at a low temperature, e.g. around −30° C. to around ambient temperature, optionally in the presence of a base, e.g. an organic base such as an amine, e.g. triethylamine, pyridine, or dimethylaminopyridine, or a cyclic amine, such as N-methylmorpholine.

Where an acid $R^3CO_2H$ is used, the reaction may additionally be performed in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively, the acid may be reacted with a chloroformate, for example ethylchloroformate, prior to reaction with the amine of formula (4).

Similar reaction conditions and reagents may be used to generate an intermediate ester of formula (3) in which $R^1$ is a —$CONHR^3$ group, from an amine $R^3NH_2$ or a salt thereof, and an acid $Ar^1(Alk^a)_rL^1Ar^2CH(CO_2H)C(R^a)(R^{a'})CO_2R^g$ or an active derivative thereof. Equally, similar reaction conditions and reagents may be used to obtain an ester of formula (3) in which $R^1$ is a —$NHC(O)OR^3$ group from an amine of formula (4) and an appropriate chloroformate $ClCO_2R^3$.

Esters of formula (3) in which $R^1$ is a —$NHCSR^3$ or —$CSNHR^3$ group may be prepared by treating a corresponding ester in which $R^1$ is a —$NHCOR^3$ or —$CONHR^3$ group with a thiation reagent, such as Lawesson's Reagent, in an anhydrous solvent, for example a cyclic ether such as tetrahydrofuran, at an elevated temperature such as the reflux temperature.

This reaction may not be particularly suitable with starting materials in which other carbonyl groups are present, for example in $Ar^1$, $Ar^2$ and/or $R^3$, and which might undesirably participate in the reaction. To avoid this the reaction with the thiation reagent may be performed earlier in the synthesis of the compound of the invention with an intermediate in which other carbonyl groups are absent and any required carbonyl groups then subsequently introduced by for example acylation as generally described hereinafter.

Intermediate esters of formula (3) in which $R^1$ is a —$NHCONHR^3$ or —$NHCSNHR^3$ group may be prepared from the corresponding amine of formula (4) by reaction with an isocyanate $R^3NCO$ or isothiocyanate $R^3NCS$. The reaction may be performed in a solvent such as acetonitrile or an ether at an elevated temperature, e.g. the reflux temperature.

Amines of formula (4) may also be used to obtain intermediate esters of formula (3) in which $R^1$ is a —$NHSO_2R^3$ group by reaction with a reagent $R^3SO_2L^6$ (where $L^6$ is a leaving group such as a halogen atom, e.g. a bromine, iodine or chlorine atom) in the presence of a base, for example an inorganic base such as sodium hydride, in a solvent such as an amide, e.g. a substituted amide such as dimethylformamide, at for example ambient temperature.

Intermediate esters of formula (3) in which $R^1$ is a —$NHR^3$ group may be prepared by coupling an amine of formula (4) with a reagent $R^3X^2$ in which $X^2$ is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluenesulphonyloxy group.

The coupling reaction may be carried out using standard conditions for reactions of this type. Thus for example the reaction may be carried out in a solvent, for example an alcohol, e.g. methanol or ethanol, at a temperature from around ambient to the reflux temperature, optionally in the presence of a base such as an amine, e.g. triethylamine or N,N-diisopropylethylamine, or a cyclic amine, such as N-methylmorpholine or pyridine.

The intermediate amines of formula (4) may also be used to obtain esters of formula (3) in which $R^1$ is a —$NHSO_2NHR^3$ group by reaction with a sulphamide $R^3NHSO_2NH_2$ in the presence of an organic base such as pyridine at an elevated temperature, e.g. the reflux temperature.

In a further example compounds of the invention may be obtained from resin linked (e.g. Wang resin) amino acids e.g.

suitably N-protected e.g. fluorenylmethoxycarbonyl protected aryl amino acids. Resin linked amines of formula (4) ($R^g$ represents the resin linker) may be obtained for example by reduction of the nitro [—$NO_2$] group of suitable resin linked amino acids e.g. nitroaryl amino acids with for example a tin reagent e.g. stannous chloride in a solvent such as an amide e.g. a substituted amide such as dimethylformamide at for example ambient temperature, followed by reaction of the newly generated amino (—$NH_2$) group with for example an acid chloride $Ar^1(Alk^a)_rCOCl$ or an isocyanate $Ar^1(Alk^a)_rNCO$ optionally in the presence of an organic base e.g. an amine such as diisopropylethylamine is a solvent such as a halogenated hydrocarbon e.g. dichloromethane, at for example ambient temperature, followed by N-deprotection with for example an organic amine e.g. piperidine in a solvent such as an amide e.g. a substituted amide such as dimethylformamide. Resin linked compounds of formula (3) may be obtained by reaction of resin linked compounds of formula (4) with for example an acid ($R^3CO_2H$), isocyanate ($R^3NCO$), isothiocyanate ($R^3NCS$), sulphonyl halide ($R^3SO_2L^6$) or halide ($R^3X$) as previously described for the preparation of esters of formula (3). Compounds of the invention may be obtained from resin-linked compounds of formula (3) by cleavage from the resin with for example an organic acid, e.g. trifluoroacetic acid in an organic solvent, for example a halogenated hydrocarbon e.g. dichloromethane.

The amines of formula (4) may be obtained from simpler, known compounds by one or more standard synthetic methods employing substitution, oxidation, reduction or cleavage reactions as described below and in the Examples hereinafter. Particular substitution approaches include conventional alkylation, arylation, heteroarylation, acylation, thioacylation, halogenation, sulphonylation, nitration, formylation and coupling procedures, including for example those just described to obtain esters of formula (3). It will be appreciated that these methods may also be used to obtain or modify other compounds of formulae (1) and (2) where appropriate functional groups exist in these compounds. Additionally, although a number of the $R^3$ containing intermediates and the acid $Ar^1(Alk^a)_rL^1Ar^2CH(CO_2H)C(R^a)(R^a)CO_2R^g$ for use in the coupling reactions described above are known, others can be derived therefrom using these standard synthetic methods.

Thus compounds of the invention and intermediates thereto may be prepared by alkylation, arylation or heteroarylation. For example, compounds containing a -$L^2$H, or -$L^3$H group (where $L^2$ and $L^3$ is each a linker atom or group) may be treated with reagent $(R^4)_uL^3Alk^3X^2$ or $R^{4a}X^2$ respectively in which $X^2$ is as previously described and $R^{4a}$ is an alkyl group.

The reaction may be carried out in the presence of a base such as a carbonate, e.g. cesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydro-furan.

In another example, compounds containing a -$L^2$H or -$L^3$H group as defined above may be functionalised by acylation or thioacylation, for example by reaction with one of the alkylating agents just described but in which $X^2$ is replaced by a —$C(O)X^3$, $C(S)X^3$, —$N(R^5)COX^3$ or —$N(R^5)C(S)X^3$ group in which $X^3$ is a leaving atom or group as described for $X^2$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation or thioacylation may be carried out under the same conditions with an acid or thioacid (for example one of the alkylating agents described above in which $X^2$ is replaced by a —$CO_2H$ or —COSH group) in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction In a further example compounds may be obtained by sulphonylation of a compound containing an —OH group by reaction with one of the above alkylating agents but in which $X^2$ is replaced by a —S(O)Hal or —$SO_2$Hal group in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a -$L^2$H or -$L^3$H group as defined above may be coupled with one of the alkylation agents just described but in which $X^2$ is replaced by an —OH group in a solvent such as tetrahydrofuran in the presence of a phosphine, e.g. triphenylphosphine and an activator such as diethyl, diisopropyl- or dimethylazodicarboxylate.

In a further example, ester groups —$CO_2R^5$ or —$CO_2Alk^1$ in the compounds may be converted to the corresponding acid [—$CO_2H$] by acid- or base-catalysed hydrolysis depending on the nature of the groups $R^5$ or $Alk^1$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a further example, —$OR^5$ or —$OR^{14}$ groups [where $R^5$ or $R^{14}$ each represents an alkyl group such as methyl group] in compounds of formula (1) may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —$OCH_2R^{14}$ group (where $R^{14}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [—$CO_2Alk^1$ or $C_{O2}R^5$] or aldehyde [—CHO] by reduction, using for example a complex metal hydride such as lithium aluminium hydride or sodium borohydride in a solvent such as methanol.

In another example, alcohol —OH groups in the compounds may be converted to a corresponding —$OR^5$ group by coupling with a reagent $R^5OH$ in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NH_2$] groups in the compounds may be obtained, in another example, by reaction of a corresponding amine [—$NH_2$] with sulphamide in the presence of an organic base such as pyridine at an elevated temperature, e.g. the reflux temperature.

In a further example amine (—NH$_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—NH$_2$] groups in compounds of formula (1) may be obtained by hydrolysis from a corresponding imide by reaction with hydrazine in a solvent such as an alcohol, e.g. ethanol at ambient temperature.

In another example, a nitro [—NO$_2$] group may be reduced to an amine [—NH$_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

Aromatic halogen substituents in the compounds may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyldisulphide as the electrophile.

In another example, sulphur atoms in the compounds, for example when present in a linker group L$^2$ or L$^3$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

Chromatography, recrystalliation and other conventional separation procedures may also be used with intermediates or final products where it is desired to obtain a particular geometric isomer of the invention.

The following Examples illustrate the invention. All temperatures are in ° C. The following abbreviations are used:

| | |
|---|---|
| NMM—N-methylmorpholine; | EtOAc—ethyl acetate; |
| BOC—butoxycarbonyl; | Ar—aryl; |
| Me—methyl; | THF—tetrahydrofuran; |
| DMSO—dimethylsulphoxide; | app—apparent |
| tBu—tertiary butyl; | HOBT—1-hydroxybenzotriazole |
| DIEA—Diisopropylethylamine; | MeOH—methanol |
| EDC—1-(3-dimethylaminopropyl)-3-ethylcarbodiimide; | |
| EtOH—ethanol; | DMF:—dimethylformamide; |
| DCM:—dichloromethane; | TFA—trifluoroacetic acid |

All NMR's were obtained at 300 MHz.

INTERMEDIATE 1

3-Amino-3-(4-nitrophenyl)propanoic acid

To a hot solution of sodium ethoxide prepared from sodium (9.33 g, 405 mmol) and EtOH (330 ml) was added a hot solution of hydroxylamine hydrochloride (28.17 g, 405 mmol) in water (18 ml). A white precipitate was formed immediately. The mixture was cooled rapidly and the solid removed by filtration and washed with EtOH (40 ml). The filtrate was then returned to the reaction flask and 4-nitrocinnamic acid (30 g, 155 mmol) was added. The mixture was heated to reflux overnight. The resulting mixture was cooled to 0° and the precipitate filtered off and the solid washed with EtOH (50 ml), water (50 ml) and finally EtOH (50 ml) to give the title compound as a pale yellow solid (16 g, 49%). δH (D$_2$O) 8.31 (2H, d, J 8.7 Hz, ArH), 7.69 (2H, d, J 8.7 Hz, ArH), 4.81 (1H, app. dd. J 7.2, 7.1 C$\underline{H}$NH$_2$), 2.94 (1H, dd, J 16.4, 7.7 Hz, C$\underline{H}_A$H$_B$) and 2.86 (1H, dd, J 16.4 and 6.7 Hz, CH$_A\underline{H}_B$); m/z (ES$^+$, 60V) 211 (MH$^+$).

INTERMEDIATE 2

Methyl-3-amino-3-(4-nitrophenyl)propanoate

Intermediate 1 (5 g, 23.8 mmol) was added to a solution of acetyl chloride (5 ml) in MeOH (125 ml). The resulting solution was stirred at room temperature overnight. The solvents were then removed in vacuo and the resulting solid was triturated with hot ether, collected by filtration and washed with more ether to leave the title compound as a pale yellow powder (5.35 g, 100%). δH (D$_2$O) 8.32 (2H, d, J 8.9 Hz, ArH), 8.75 (2H, d, J 8.9 Hz, ArH), 4.90 (1H, dd, J 7.2, 6.9 Hz, C$\underline{H}$NH$_2$), 3.70 (3H, s, CO$_2$Me), 3.19 (1H, dd, J 17.1, 7.5 Hz, C$\underline{H}_A$H$_B$) and 3.09 (1H, dd, J 17.1, 6.6 Hz, CH$_A\underline{H}_B$); m/z (ES$^+$, 60V) 225 (MH$^+$).

INTERMEDIATE 3

Methyl-3-(t-butyloxycarbonylamino)-3-(4-nitrophenyl)propanoate

A solution of di-tert-butyl dicarbonate (6.58 ml, 28.6 mmol) in THF (50 ml) was added dropwise to a stirred solution of Intermediate 2 (5.35 g, 23.8 mmol) and sodium hydrogen carbonate (4.19 g, 49.9 mmol) in THF (100 ml) and water (100 ml). The mixture was stirred overnight at room temperature. The THF was then removed in vacuo and the aqueous residue extracted with EtOAc (75 ml×3). The combined organics were then washed with 10% aqueous citric acid (100 ml) and brine (100 ml), dried (Na$_2$SO$_4$) and evaporated under reduced pressure. The oil obtained was taken up in hot ether. The solution was then cooled to yield a white precipitate which was collected by filtration and washed with hexane to give the title compound (6.69 g, 87%). δH (CDCl$_3$) 8.20 (2H, d, J 8.7 Hz, ArH), 7.47 (2H, d, J 8.7 Hz, ArH), 5.71 (1H, brs, NH), 5.17 (1H, app brs, CHNH), 3.63 (3H, s, CO$_2$Me), 2.87 (2H, app. br d J 5.6 Hz, CH$_2$) and 1.42 (9H, s, $^t$Bu); m/z (ES$^+$, 60V) 347 (M$^+$+Na).

INTERMEDIATE 4

Methyl-3-(4-aminophenyl)-3-(t-butyloxycarbonylamino)propanoate

A solution of Intermediate 3 (5.6 g, 17.3 mmol) and tin (II) chloride dihydrate (19.6 g, 86.5 mmol) in EtOH (100 ml) was stirred overnight at room temperature. The EtOH was then removed in vacuo and the residue partitioned between DCM (250 ml) and saturated aqueous NaHCO$_3$ (100 ml). The resulting solid precipitate was removed by filtration and washed with copious DCM. The filtrate was then separated and the aqueous extracted with DCM(3×100 ml). The combined organics were finally washed with brine (150 ml), dried (Na$_2$SO$_4$) and evaporated under reduced pressure. Purification of the residue by column chromatography (SiO$_2$; DCM/EtOAc, 4:1) gave the title compound as a yellow oil (3.77 g, 74%) δH (DMSO-d$^6$) 7.20 (1H, br d, J 8.5 Hz, CONH), 6.93 (2H, d, J 8.4 Hz, ArH), 6.47 (2H, d, J 8.4 Hz, ArH), 5.00 (2H, br s, NH$_2$), 4.74 (1H, m, ArCH), 3.52 (3H, s, CO$_2$Me), 2.67 (1H, dd, J 15.1, 8.4 Hz, CH$_A$H$_B$CO$_2$Me), 2.56 (1H, dd, J 15.1, 6.8 Hz, CH$_A$H$_B$CO$_2$Me) and 1.33 (9H, s, tBu). m/z (ES$^+$, 60V) 295 (MH$^+$).

INTERMEDIATE 5

Methyl-3-(tert-butyloxycarbonylamino)-3-{4-[3,5-dichloroisonicotinoyl)amino]phenyl}propanoate To a solution of Intermediate 4 (3.77 g, 12.8 mmol) in DCM (50 ml) was added NMM (1.55 ml, 14.1 mmol) and a solution of 3,5-dichloroisonicotinoyl chloride (prepared by the methods detailed in International Patent Application WO99/35163) (2.97 g, 14.1 mmol) in DCM (2 ml). The reaction mixture was stirred for 3 h and then diluted with DCM (200 ml) and washed with water (2×75 ml) and brine (75 ml), dried (Na$_2$SO$_4$) and evaporated under reduced pressure. Purification of the residue by column chromatography (SiO$_2$; DCM/EtOAc, 4:1) gave the title compound as a white solid (4.7 g, 81%). δH (CDCl$_3$) 8.93 (1H, br s, NH), 8.51 (2H, s, ArCl$_2$H), 7.33 (2H, d, J 8.3 Hz, ArH), 7.13 (2H, d, J 8.3 Hz, ArH), 5.75 (1H, br s, NHBoc), 4.90 (1H, app. dd, J 14.2, 6.0 Hz, CHNH), 3.61 (3H, s, CO$_2$Me), 2.75 (2H, d, J 6.0 Hz, CH$_2$) and 1.35 (9H, s $^t$Bu); m/z (ES$^+$, 60V) 490 (M$^+$+Na).

INTERMEDIATE 6

Methyl-3-amino-3-{4-[(3,5-dichloroisonicotinoyl) amino]phenyl}propanoate trifloroacetic acid salt To a solution of Intermediate 5 (4.7 g, 10.3 mmol) in DCM (100 ml) and water (0.5 ml) was added TFA (1.59 ml, 20.6 mmol) dropwise. The mixture was stirred at room temperature for 4 h. The volatiles were then removed in vacuo and the resulting yellow oil triturated with hexane/ether (~1:2) to give a sticky semi-solid. A small amount of EtOAc was then added and the solution heated to produce a white solid. The solution was then cooled, filtered and the solid washed with ether to leave the title compound (4.9 g, 100%) as a white solid. δH (D$_2$O) 8.69 (2H, s, ArCl$_2$H), 7.72 (2H, d, J 8.4 Hz, ArH), 7.59 (2H, d, J 8.4 Hz, ArH), 4.91 (1H, dd, J 7.2, 7.2 Hz, CH), 3.75 (3H, s, CO$_2$Me), 3.30 (1H, dd, J 16.9, 7.5 Hz, CH$_A$H$_B$) and 3.21 (1H, dd, J 16.9, 7.0 Hz, CH$_A$H$_B$); m/z (ES$^+$, 60V) 368 (MH$^+$).

INTERMEDIATE 7

N-(3,5-Dichlorobenzenesulphonyl)-L-proline methyl ester 3,5-Dichlorobenzenesulphonyl chloride (5.0 g, 20.36 mmol) was added portionwise over 30 min to a solution of L-proline methyl ester hydrochloride (3.69 g, 22.4 mmol) and DIEA (7.8 ml, 44.8 mmol) in DCM (100 ml) at 0°. The reaction mixture was stirred overnight at room temperature then concentrated in vacuo. The residue was dissolved in EtOAc (100 ml) and washed with saturated aqueous NaHCO$_3$ (100 ml), citric acid (10%, 100 ml) and saturated aqueous NaHCO$_3$ (100 ml). The organic phase was dried (MgSO$_4$) and concentrated in vacuo. Column chromatography (SiO$_2$, EtOAc/hexane, 80:20) gave the title compound (3.77 g). δH (CDCl$_3$) 7.8 (2H, d, J 2.0 Hz, ArH), 7.5 (1H, d, J 2.0 Hz, ArH), 4.4 (1H, m, CHα), 3.7 (3H, s, CO$_2$Me), 3.4 (2H, m, CH$_2$N), 2.0 (4H, m, NCH$_2$CH$_2$CH$_2$); m/z (ES$^+$, 70V), 338 (MH$^+$).

INTERMEDIATE 8

N-(3,5-Dichlorobenzenesulphonyl)-L-proline

Lithium hydroxide monohydrate (555 mg, 13.24 mmol) was added to Intermediate 7 (3.73 g, 11.03 mmol) in THF (25 ml) and water (25 ml). The mixture was stirred at room temperature overnight then concentrated in vacuo. Water was added to the residue and the pH adjusted to pH1 with 1.0M HCl. The resulting precipitate was filtered off, washed with water and dried to give the title compound as a white solid (3.48 g). δH (CDCl$_3$) 7.8 (2H, s, ArH), 7.6 (1H, s, ArH), 4.4 (1H, m, CHα), 3.6 (1H, m, NCH$_A$H$_B$), 3.5 (1H, m, NCH$_A$H$_B$), 2.0 (4H, m, NCH$_2$CH$_2$CH$_2$); m/z (ES$^+$, 70V) 324 (MH$^+$).

INTERMEDIATE 9

Ethyl (2RS,3RS)-3-azido-2-hydroxy-3-(4-nitrophenyl)propanoate

A mixture of ethyl (2RS,3RS)-3-(4-nitrophenyl-2-oxirane carboxylate [prepared by the method of Moyna, G., Williams, H. J., Scott, A. I., Synth. Commun, (1996) 26, 2235–9] (2.5 g, 10.5 mmol) sodium azide (3.4 g, 52.5 mmol), ethyl formate (10 ml) in EtOH/water (8:1, 50 ml) was heated at 50° overnight. The mixture was diluted with EtOAc, washed with water and brine, dried (Na$_2$SO$_4$) and evaporated in vacuo. Column chromatography (SiO$_2$; MeOH/DCM, 1:99) gave the title compound as a yellow oil (2.34 g) (less polar regioisomer). δH (CDCl$_3$) 8.24 (2H, d, J 8.8 Hz, ArH), 7.55 (2H, d, J 8.9 Hz, ArH), 5.02 (1H, d, J 3.7 Hz, CHN$_3$), 4.57 (1H, dd, J 5.3, 3.7 Hz, CHOH), 4.25–4.14 (2H, m, CO$_2$CH$_2$), 3.15 (1H, d, J 5.5 Hz, OH), 1.21 (3H, t, J 7.2 Hz, CO$_2$CH$_2$CH$_3$). m/z (ES$^+$, 70V) 253 (M$^+$–N$_2$).

INTERMEDIATE 10

Ethyl (2RS,3RS)-3-amino-3-(4-aminophenyl)-2-hydroxypropanoate

A mixture of Intermediate 9 (1.38 g, 4.93 mmol) and palladium on charcoal (10% wt, Pd, 140 mg) in EtOH (50 ml) was stirred under a hydrogen atmosphere (balloon) at room temperature overnight. The catalyst was filtered off and the filtrate concentrated in vacuo to give the title compound as a yellow gum (1.10 g) δH (DMSO-d$^6$) 6.93 (2H, d, J 8.4 Hz, ArH), 6.44 (2H, d, J 8.4 Hz, ArH), 4.00 (2H, q, J 7.1 Hz, CO$_2$CH$_2$CH$_3$), 4.00 (1H, CHNH$_2$), 3.82 (1H, d, J 6.0 Hz, CHOH), 1.12 (3H, t, J 7.1 Hz, CO$_2$CH$_2$CH$_3$), 4.80 (2H, br s, ArNH$_2$), 3.30 (2H, v br s, CHNH$_2$), 1.90 (1H, v br s, OH); m/z (ES$^+$, 70V) 208 (M$^+$–NH$_3$).

INTERMEDIATE 11

3-(9-Fluorenylmethoxycarbonylamino)-3-(4-nitrophenyl)propanoic acid

A cold (0°) solution of 3-amino-3-(4-nitrophenyl) propanoic acid (3.2 g, 15 mmol) in 10% aqueous sodium carbonate (60 ml) and 1,4-dioxan (30 ml) was treated portion-wise with 9-fluorenylmethoxycarbonyl-N-hydroxysuccinimide (5.6 g, 17 mmol) in 1,4-dioxan (15 ml) and the mixture stirred at room temperature for 12 h. The mixture was poured into water (300 ml) and the aqueous phase washed 3 times with ether. The aqueous layer was then acidified with solid citric acid and extracted into ether. The combined organic layers were dried (MgSO$_4$) and evaporated to a yellow oil then triturated from hexane and EtOAc to afford the title compound as a yellow solid (2.83 g); m/z (ES$^+$, 70V) 432 (MH$^+$).

INTERMEDIATE 12

Resin bound 3-(9-Fluorenylmethoxycarbonylamino)-3-(4-aminophenyl)propanoic acid Wang resin (Advanced Chemtech, 2.5 g, 0.8 mmol/g, 2 mmol equivalent) in a mixture of DMF (20 ml) and DCM (20 ml) was treated with 3-(9-fluorenylmethoxycarbonylamino)-3-(4-nitrophenyl) propanoic acid (2.6 g, 6 mmol), 4-dimethylaminopyridine (244 mg, 2 mmol) and 1,3-diisopropylcarbodiimide (940 μl, 6 mmol) and the mixture agitated under nitrogen at room temperature for 24 h. The resin was filtered and washed with DMF and DCM. The resin was treated with a 1M solution of stannous chloride dihydrate in DMF (50 ml) at room temperature for 8 h then washed as before to give the title compound.

INTERMEDIATE 13

Resin bound 3-{4-[(3,5-dichloroisonicotinoyl) amino]phenyl}-3-aminopropanoic acid Intermediate 12 (3.3 g, 0.28 mmol/g, 0.9 mmol equivalent) was treated with DIEA (1.6 ml, 9 mmol) and 3,5-dichloro-4-pyridinecarbonyl chloride (1.9 g, 9 mmol) in DCM (20 ml) with agitation at room temperature for 12 h. The resin was filtered and washed with DMF and DCM followed by treatment with a 20% solution of piperidine in DMF (40 ml) for 40 min at room temperature then filtered and washed as before to afford the title compound.

INTERMEDIATE 14

Resin bound 3-{4-[(2,6-dichlorobenzoyl)amino] phenyl}-3-aminopropanoic acid

Intermediate 14 was prepared in a similar manner to Intermediate 13 from Intermediate 12, using 2,6-dichlorobenzoylchloride for 8 h.

EXAMPLE 1

Methyl-3-[(2-chloronicotinoyl)amino]-3-{4-[(3,5-dichloroisonicotinoyl)amino]phenyl}propanoate To a suspension of Intermediate 6 (600 mg, 1.24 mmol) in DCM (25 ml) was added 2-chloronicotinic acid (195 mg, 1.24 mmol), NMM (287 μl, 2.61 mmol), HOBT (190 mg, 1.37 mmol) and EDC (267 mg, 1.37 mmol). The resulting solution was stirred overnight at room temperature and then diluted with DCM (100 ml) and washed with saturated aqueous NaHCO$_3$ (50 ml), water (50 ml) and brine (50 ml), dried (Na$_2$SO$_4$) and evaporated under reduced pressure. The residue was then purified by column chromatography (SiO$_2$, DCM/MeOH, 95:5) to give the title compound as a creamy solid. δH (DMSO-$^6$) 9.18 (1H, d, J 8.4 Hz, NH), 8.79 (2H, s, ArCl$_2$H), 8.46 (1H, dd, J 4.8, 1.8 Hz, ArClH), 7.82 (1H, dd, J 7.5, 1.8 Hz, ArClH), 7.62 (2H, d, J 8.5 Hz, ArH), 7.49 (1H, dd, J 7.5, 4.8 Hz, ArClH), 7.41 (2H, d, J 8.5 Hz, ArH), 5.45–5.37 (1H, m, CH), 3.60 (3H, s, OMe) and 2.86 (2H, d, J 8.0 Hz, CH$_2$); m/z (ES$^+$, 60V) 507 (MH$^+$).

EXAMPLE 2

3-[(2-Chloronicotinoyl)amino]-3-{4-[(3,5-dichloroisonicotinoyl)-amino]phenyl}propanoic acid The compound of Example 1 (340 g, 0.67 mmol) was dissolved in a mixture of THF (5 ml) and water (5 ml). Lithium hydroxide monohydrate (31 mg, 0.74 mmol) was added and the mixture stirred at room temperature for 3 h. The THF was removed under reduced pressure and the aqueous residue acidified with aqueous HCl (1M). The resulting white precipitate was collected by filtration and washed well with water. Freeze drying from a mixture of MeOH and water gave the title compound as a white solid (193 mg, 58%). δH (DMSO-d$^6$) 12.30 (1H, br s CO$_2$H), 10.91 (1H, s, NH), 9.12 (1H, d, J 8.2 Hz, NH), 8.79 (1H, s, ArCl$_2$H), 8.46 (1H, dd, J 4.8, 1.9 Hz, ArClH), 7.81 (1H, dd, J 7.5, 1.9 Hz, ArClH), 7.61 (2H, d, J 8.5 Hz, ArH), 7.49 (1H, dd, J 7.5, 4.8 Hz, ArClH), 7.41 (2H, d, J 8.5 Hz, ArH), 5.38–5.31 (1H, m, CH) and 2.84–2.69 (2H, m, CH$_2$); m/z (ES$^+$, 60V) 493 (MH$^+$).

EXAMPLE 3

Methyl-3-(3,5-dichloroisonicotinoylamino)-3-{4-[(3,5-dichloroisonicotinoyl)amino]phenyl}propanoate To a suspension of Intermediate 6 (600 mg, 1.24 mmol) in DCM (25 ml) was added NMM (287 μl, 2.61 mmol) followed by 3,5-dichloroisonicotinoyl chloride (272 mg, 1.36 mmol). The mixture was stirred for 2 h and then diluted with DCM (100 ml) and washed with water (2×50 ml) and brine (50 ml), dried (Na$_2$SO$_4$) and evaporated under reduced pressure. The residual peach foam was purified by column chromatography (SiO$_2$, DCM/MeOH, 92:8) to give the title compound as a pale cream oil (629 mg, 94%). δH (CDCl$_3$) 9.01 (1H, s, NH), 8.41 (2H, s, ArCl$_2$H), 8.39 (2H, s, ArCl$_2$H), 7.73 (1H, d, J 8.2 Hz, NH), 7.44 (2H, d, J 8.5 Hz, ArH), 7.28 (2H, d, J 8.5 Hz, ArH), 5.49 (1H, dd, J 8.0, 6.4 Hz, CH), 3.62 (3H, s, Me), 2.94 (1H, dd, J 16.1, 6.6 Hz, CH$_A$H$_B$) and 2.86 (1H, dd, J 16.1, 6.2 Hz, CH$_A$H$_B$); m/z (ES$^+$ 60V) 241 (MH$^+$).

EXAMPLE 4

3-[(3,5-Dichloroisonicotinoyl)amino]-3-{4-[(3,5-dichloroisonicotinoyl)amino]phenyl}propanoic acid The title compound was prepared by the method of Example 2 from the compound of Example 3 as a pale cream solid (356 mg, 58%). δH (DMSO d⁶) 10.92 (1H, s, NH), 9.41 (1H, d, J 8.1 Hz, NH), 8.78 (2H, s, ArCl$_2$H), 8.68 (2H, s, ArH), 5.37 (1H, app. q. J 7.4 Hz, CH) and 2.75 (2H, d, J 7.4 Hz, CH$_2$); m/z (ES⁺, 60V) 527 (MH⁺).

EXAMPLE 5

Methyl-3-{4-[(3,5-dichloroisonicotinoyl)amino]phenyl}-3-[(2,6-dimethoxybenzoyl)amino]propanoate To a suspension of Intermediate 6 (600 mg, 1.24 mmol) in DCM (25 ml) was added NMM (287 ml, 2.61 mmol) and 2,6-dimethoxybenzoyl chloride (23 mg, 1.36 mmol). The reaction mixture was stirred for a further 2 h and then diluted with DCM (100 ml) and washed with water (2×100 ml) and brine (1×100 ml), dried (Na$_2$SO$_4$) and evaporated under reduced pressure. The resulting semi-solid was purified by column chromatography (SiO$_2$, DCM/MeOH, 92:8) to give the title compound as a pale cream oil (658 mg, 100%). δH (CDCl$_3$) 8.48 (2H, s, ArCl$_2$H), 8.38 (1H, s, NH), 7.55 (2H, d, J 8.6 Hz, ArH), 7.39 (2H, d, J 8.6 Hz, ArH), 7.28 (1H, t, J 8.4 Hz, Ar(OMe)$_2$H), 6.91 (1H, d, J 8.6 Hz, NH), 6.55 (2H, d, J 8.4 Hz, Ar(OMe)$_2$H), 5.60–5.30 (1H, m, CH), 3.78 (6H, s, OMe×2), 3.63 (3H, s, CO$_2$Me), 3.01 (1H, dd, J 16.0, 5.7 Hz, CH$_A$H$_B$) and 2.93 (1H, dd, J 16.0, 5.7 Hz, CH$_A$H$_B$); m/z (ES⁺, 60V) 532 (MH⁺).

EXAMPLE 6

3-{4-[(3,5-Dichloroisonicotinoyl)amino]phenyl}-3-[(2,6-dimethoxybenzoyl)amino]propanoic acid The title compound was prepared by the method of Example 2 from the compound of Example 5 as a white solid (270 mg, 42%). δH (DMSO-d⁶) 10.84 (1H, s, NH), 8.77 (2H, s, ArCl$_2$H), 8.50–8.40 (1H, m, NH), 7.58 (2H, d, J 8.5 Hz, ArH), 7.40 (2H, d, J 8.5 Hz, ArH), 7.27 (1H, t, J 8.4 Hz, Ar(OMe)$_2$H), 6.64 (2H, d, J 8.4 Hz, Ar(OMe)$_2$H), 5.30 (1H, app. q, J 7.5 Hz, CH), 3.10 (6H, s, OMe), 2.72 (1H, dd, J 15.4, 7.0 Hz, CH$_A$H$_B$) and 2.65 (1H, dd, J 15.4, 7.2 CH$_A$H$_B$); m/z (ES⁺, 60V) 518 (MH⁺).

EXAMPLE 7

Methyl-3-{4-[(dichloroisonicotinoyl)amino]phenyl}-3-(4,6-dimethoxy-1,3,5-triaz-2-ylamino)propanoate Intermediate 6 (1.0 g, 2.07 mmol) was partitioned between EtOAc (100 ml) and saturated aqueous NaHCO$_3$ solution (100 ml). The phases were thoroughly shaken and then separated and the aqueous layer extracted with EtOAc (2×100 ml). The combined organic phases were dried (Na$_2$SO$_4$) and evaporated to leave the free amine. A solution of the amine (626 mg, 1.70 mmol) 2-chloro-4,6-dimethoxy-1,3,5-triazene (404 mg, 2.30 mmol) and NMM (233 μl, 2.30 mmol) in MeOH was stirred overnight at 60°. The MeOH was removed in vacuo and the residue partitioned between EtOAc (100 ml) and saturated aqueous NaHCO$_3$ (100 ml). The phases were separated and the aqueous layer extracted with EtOAc (2×75 ml). The combined organics were then washed with 5% aqueous citric acid (50 ml), saturated aqueous NaHCO$_3$ (50 ml) and brine (50 ml), dried (Na$_2$SO$_4$) and evaporated under reduced pressure. The residue was purified by column chromatography (SiO$_2$, DCM/MeOH, 92:8) to give the title compound as a cream foam (370 mg, 43%) δH (CDCl$_3$) 9.29 (H, s, NH), 8.38 (2H, s, ArCl$_2$H), 7.54 (2H, d, J 8.5 Hz, ArH), 7.28 (2H, d, J 8.5 Hz, ArH), 6.81 (1H, d, J 8.4 Hz, NH), 5.53 (1H, dd, J 6.7, 6.2 Hz, CH), 3.85 (3H, s, OMe), 3.83 (3H, s, OMe), 3.59 (3H, s, CO$_2$Me), 2.96 (1H, dd, J 16.8, 6.7 Hz, CH$_A$H$_B$) and 2.84 (1H, dd, J 16.8, 6.2 Hz, CH$_A$H$_B$); m/z (ES⁺, 60V) 529 (M⁺+Na).

EXAMPLE 8

3-{4-[(3,5-Dichloroisonicotinoyl)amino]phenyl}-3-(4,6-dimethoxy-1,3,5-triaz-2-ylamino)propanoic acid The title compound was prepared by the method of Example 2 from the compound of Example 7 as a white powder (170 mg, 47%). δH (DMSO-d⁶) 10.89 (1H, s, NH), 8.48 (2H, s, ArCl$_2$H), 8.49 (1H, d J 8.3 Hz, NH), 7.58 (2H, d, J 8.5 Hz, ArH), 7.40 (2H, d, J 8.5 Hz, ArH), 5.36 (1H, ddd, J 8.6, 8.3, 6.4 Hz, CH), 3.80 (6H, s, OMe), 2.87 (1H, dd, J 15.9, 8.6 Hz, CH$_A$H$_B$) and 2.70 (1H, dd, J 15.9, 6.0 Hz, CH$_A$H$_B$); m/z (ES⁺, 60V) 493. (MH⁺).

EXAMPLE 9

Methyl 3-{4-[(3,5-dichloroisonicotinoyl)amino]phenyl}-3-{[6-(propylsulphonyl)-4-pyrimidinyl]amino}propanoate A mixture of Intermediate 6 (502 mg, 1.00 mmol) 4,6-bis(propylsulphonyl) pyrimidine (prepared from 4,6-dichloropyrimidine, propanethiol and sodium hydride in THF) (321 mg, 1.10 mmol) and DIEA (348 μl, 2.00 mmol) in acetonitrile (3 ml) was heated at 500 overnight. The mixture was diluted with DCM, washed with dilute HCl, dried (Na$_2$SO$_4$) and evaporated in vacuo. Column chromatography (SiO$_2$: MeOH/DCM, 6:94) gave the title compound as a white foam (344 mg). δH (DMSO-d⁶) 10.91 (1H, s, CONH), 8.77 (2H, s, Cl$_2$PyH), 8.70 (1H, d, J 7.9 Hz, NH), 8.57 (1H, s, ArH), 7.61 (2H, d, J 8.6 Hz, ArH), 7.40 (2H, d, J 8.5 Hz, ArH), 7.12 (1H, s, ArH), 5.55 (1H, m, CHNH), 3.56 (3H, s, CO$_2$Me), 3.36–3.32 (2H, m, SO$_2$CH$_2$), 2.93–2.89 (2H, m, CH$_2$CO$_2$), 1.63–1.55 (2H, m, SO$_2$CH$_2$CH$_2$CH$_3$), 0.93 (3H, t, J 7.4 Hz, SO$_2$CH$_2$CH$_2$CH$_3$); m/z (ES⁺, 70V) 552 (MH⁺).

EXAMPLE 10

3-{4-[(3,5-Dichloroisonicotinoyl)amino]phenyl}-3-{[6-(propylsulphonyl)-4-pyrimidinyl]amino}propanoic acid The title compound was prepared by the method of Example 2 from the compound of Example 9 as a white powder. δH (DMSO-d⁶) 12.34 (1H, br s, CO$_2$H), 10.90 (1H, s, CONH), 8.77 (2H, s, Cl$_2$PyH), 8.70 (1 H. d, J 7.9 Hz, NH), 8.55 (1H, s, ArH), 7.60 (2H, d, J 8.5 Hz, ArH), 7.39 (2H, d, J 8.5 Hz, ArH), 7.12 (1H, s, ArH), 5.52 (1H, m, CHNH), 3.4 (2H, m, SO$_2$CH$_2$), 2.90–2.75 (2H, m, CH$_2$CO$_2$), 1.63–1.55 (2H, m, SO$_2$CH$_2$CH$_2$), 0.93 (3H, t, J 7.4 Hz, SO$_2$CH$_2$CH$_3$); m/z (ES⁺, 70V) 538 (MH⁺).

EXAMPLE 11

Methyl 3-[(4-chloro-6-methoxy-1,3,5-triazin-2-yl)amino]-3-{(4-[(3,5-dichloroisonicotinoyl)amino]phenyl}propanoate A solution of dichloromethoxy-1,3,5-triazine (396 mg, 2.2 mmol) in acetonitrile (5 ml) was added to a mixture of Intermediate 6 (1.004 g, 2 mmol) and diisopropylethylamine (732 μl, 4.2 mmol) in acetonitrile (5 ml) at 0°. After 30 min the mixture was diluted with DCM, washed with dilute HCl, dried (Na$_2$SO$_4$) and evaporated in vacuo. Column chromatography (SiO$_2$: EtOAc/hexane, 65:35) gave the title compound as a colourless gum (694 mg). δH (DMSO-d$^6$, 300K) (2 rotameric species observed) 10.91 (1H, s, CONH), 9.16 (d, J 8.1 Hz) and 9.08 (d, J 8.6 Hz) together (1H, CHNH), 8.78 (2H, s, PyH), 7.60 (2H, d, J 8.6 Hz, ArH), 7.40–7.37 (2H, m, ArH), 5.41–5.32 (1H, m, CHCH$_2$), 3.86 (3H, s, OMe), 3.56 (3H, s, OMe), 2.97 (1H, dd, J 16.1, 8.6 Hz, CH$_A$H$_B$CO$_2$), 2.87 (1H, m, CH$_A$H$_B$CO$_2$); m/z (ES$^+$, 70V) 511 (MH$^+$).

EXAMPLE 12

Methyl 3-{4-[(3,5-dichloroisonicotinoyl)amino]phenyl}-3-({4-[2-hydroxyethylamino]-6-methoxy-1,3,5-triazin-2-yl}amino)propanoate A mixture of the compound of Example 11 (350 mg, 0.683 mmol), DIEA (119 μl, 0.683 mmol) and ethanolamine (4.5 μl, 0.75 mmol) in THF (10 ml) was stirred at room temperature overnight. The mixture was diluted with DCM, washed with dilute HCl, dried (Na$_2$SO$_4$) and evaporated in vacuo. Column chromatography (SiO$_2$, MeOH/DCM, 10:90) gave the title compound as a colourless glass (204 mg). δH (DMSO-d$^6$) (rotameric species observed) 10.87 (1H, s, CONH), 8.77 (2H, s, PyH), 7.85–7.65 (1H, m, NH), 7.56 (2H, d, J 8.6 Hz, ArH), 7.39 (2H, m, ArH), 7.10–6.85 (1H, m, NH), 5.38 (1H, m, ArCHNH), 4.61 (1H, m, OH), 3.73–3.69 (3H, m, OMe), 3.55 (3H, s, OMe), 3.44 (2H, br s, CH$_2$CH$_2$), 3.30 (CH$_2$CH$_2$, peak under HOD), 2.95 (1H, m, CH$_A$H$_B$CO$_2$Me), 2.75 (1H, dd, CH$_A$H$_B$CO$_2$Me); m/z (ES$^+$, 70V) 536 ((MH$^+$).

EXAMPLE 13

3-{4-[(3,5-Dichloroisonicotinoyl)amino]phenyl}-3-({4-[2-hydroxyethylamino]-6-methoxy-1,3,5-triazin-2-yl}amine)propanoic acid The title compound was prepared by the method of Example 2 from the compound of Example 12 as a white solid. δH (DMSO-d$^6$, 390K) 10.40 (1H, br s, CONH), 8.66 (2H, s, Cl$_2$PyH), 7.55 (1H, br, NH), 7.52 (2H, br d, ArH), 7.41 (2H, br d, J 8.5 Hz, ArH), 6.36 (1H, br m, NH), 5.40 (1H, br m, ArCHNH), 3.76 (3H, s, OMe), 3.52 (2H, t, J 6.1 Hz, NHCH$_2$CH$_2$CH), 3.34 (2H, q, J 5.7 Hz, NHCH$_2$CH$_2$CH), 2.3 (1H, br s, OH) from 300K spectrum 2.8–2.5 (2H, m, CH$_2$CO$_2$H); m/z (ES$^+$, 70V), 522 (MH$^+$).

EXAMPLE 14

Methyl 3-{4-[(3,5-dichloroisonicotinoyl)amino]phenyl}-3-[({2S)-1-[(3,5-dichlorophenyl)sulphonyl]tetrahydro-1-H-pyrrol-2-yl}carbonyl)amino]propanoate EDC (158 mg, 0.825 mmol) was added to a mixture of Intermediate 6 (37.7 mg, 0.75 mmol) Intermediate 8 (243 mg, 0.75 mmol) HOBT (111 mg, 0.825 mmol) and NMM (173 μl, 1.58 mmol) in DMF (5 ml). The mixture was stirred at room temperature overnight then the solvent removed in vacuo. The residue was dissolved in EtOAc and washed with dilute HCl, NaHCO$_3$ (aqueous), water and brine, dried (Na$_2$SO$_4$) and evaporated in vacuo. Column chromatography (SiO$_2$: MeOH/DCM, 5:95) gave the title compound as a white foam (402 mg). δH (DMSO-d$^6$) (mixture of diastereoisomers) 10.90 (1H, s, CONH), 8.78 (2H, s, Cl$_2$PyH), 8.53 (1H, m, CHNH), both diastereoisomers), 8.00 (t, J 1.9 Hz) and 7.97 (t, J 1.9 Hz) together (1H, Cl$_2$ArH), 7.84 (d, J 1.9 Hz) and 7.78 (d, J 1.9 Hz) together (2H, Cl$_2$ArH), 7.60 (d, J 8.6 Hz) and 7.59 (d, J 8.6 Hz) together (2H, ArH), 7.36 (d, J 8.6 Hz) and 7.34 (d, J 8.6 Hz) together (2H, ArH), 5.18 (1H, m, CHNH), 4.22–4.14 (1H, m, CHα), 3.57 (3H, s, CO$_2$Me), 3.45–3.35 (1H, m, NCH$_A$H$_B$), 3.30 (1H, NCH$_A$H$_B$), 2.95–2.75 (2H, m, CH$_2$CO$_2$Me), 1.95–1.60 (4H, m, NCH$_2$CH$_2$CH$_2$); m/z (ES$^+$, 70V) 675 (MH$^+$).

EXAMPLE 15

3-{4-[(3,5-Dichloroisonicotinoyl)amino]phenyl}-3-[({(2S)-1-[(3,5-dichlorophenyl)sulphonyl]tetrahydro-1-H-pyrrol-2-yl}carbonyl)amino]propanoic acid The title compound was prepared by the method of Example 2 from the compound of Example 14 as a white solid δH (DMSO-d$^6$) (2 diastereoisomers) 12.3 (1H, br s, CO$_2$H), 10.89 (1H, s, CONH), 8.78 (2H, s, Cl$_2$PyH), 8.53 (d, J 8.1 Hz) and 8.48 (d, J 8.1 Hz) together (1H, CONH), 8.00 (t, J 1.9 Hz) and 7.97 (t, J 1.9 Hz) together (1H, ArH), 7.85 (d, J 1.8 Hz) and 7.78 (d, J 1.8 Hz) together (2H, ArH), 7.61–7.57 (2H, m, ArH), 7.37–7.32 (2H, m, ArH), 5.13 (1H, m, CHNH), 4.24–4.16 (1H, m, CHα), 3.45–3.35 (1H, m, CH$_A$H$_B$N), 3.25 (1H, CH$_A$H$_B$N), 2.81 (1H, dd, J 15.8, 7.5 Hz, CH$_A$H$_B$CO$_2$), 2.75–2.69 (1H, m, CH$_A$H$_B$CO$_2$), 1.9–1.6 (4H, m, CH$_2$CH$_2$CH$_2$N); m/z (ES$^+$, 70V) 659 (MH$^+$).

EXAMPLE 16

Ethyl (2RS,3RS)-3-{4-[(3,5-dichloroisonicotinoyl)amino]phenyl}-3-[4-(3,5-dichloroisonicotinoyl)amino]-2-hydroxypropanoate A solution of 3,5-dichloroisonicotinoylchloride (269 mg, 1.28 mmol) in DCM (5 ml) was added to a solution of Intermediate 10 (130 mg, 0.58 mmol) and NMM (140 μl, 1.28 mmol) in DCM (5 ml). After 3.5 h at room temperature the mixture was diluted with DCM and washed with dilute HCl and NaHCO$_3$ (aqueous), dried (Na$_2$SO$_4$) and evaporated in vacuo. Column chromatography (SiO$_2$; MeOH/DCM , 7:93) gave the title compound as a white solid (198 mg). δH (DMSO-d$^6$) 10.90 (1H, s, CONHAr), 9.56 (1H, d, J 9.0 Hz, CONHCH), 8.79 (2H, s, Cl$_2$PyH$_2$), 8.67 (2H, s, Cl$_2$PyH$_2$), 7.58 (2H, d, J 8.6 Hz, ArH), 7.38 (2H, d, J 8.6 Hz, ArH), 5.88 (1H, d, J 6.0 Hz, OH), 5.35 (1H, dd, J 9.0, 5.8 Hz, NHCH), 4.32 (1H, t, 1 5.9 Hz, CHOH), 4.15–4.08 (2H, m, CO$_2$CH$_2$CH$_3$), 1.22 (3H, t, J 7.1 Hz, CO$_2$CH$_2$CH$_3$). m/z (ES$^+$, 70V) 573 (MH$^+$).

EXAMPLE 17

(2RS,3RS)-3-{4-[(3,5-Dichloroisonicotinoyl)amino]phenyl}-3-[4-(3,5-dichloroisonicotinoyl)amino]-2-hydroxypropanoic acid The title compound was prepared by the method of Example 2 from the compound of Example 16 as an off white solid. δH (DMSO-d$^6$) 12.8 (1H, v br s, CO$_2$H), 10.90 (1H, s, CONHAr), 9.54 (1H, d, J 8.8 Hz, NHCH), 8.78 (2H, s, Cl$_2$PyH$_2$), 8.66 (2H, s, Cl$_2$PyH$_2$), 7.57 (2H, d, J 8.4 Hz, ArH), 7.39 (2H, d, J 8.4 Hz, ArH), 5.6 (1H, v br s, OH), 5.37 (1H, dd, J 8.7, 5.4 Hz, NHCH), 4.26 (1H, d, J 5.3 Hz, CHOH); m/z (ES$^+$, 70V) 545 (MH$^+$).

EXAMPLE 18

Ethyl (2RS,3RS)-3-(4-aminophenyl)-3-[({2S)-1-[(3,5-dichlorophenyl)sulphonyl]tetrahydro-1-H-pyrrol-2-yl}carbonyl)amino]-2-hydroxypropanoate A mixture of Intermediate 10 (250 mg, 1.12 mmol), Intermediate 8 (363 mg, 1.12 mmol), HOBT (166 mg, 1.23 mmol), NMM (135 µl, 1.23 mmol) and EDC HCl (236 mg, 1.23 mmol) in DMF (5 ml) and DCM (10 ml) was stirred at room temperature for 3 days. The solvents were removed in vacuo. The residue was dissolved in DCM, washed with dilute HCl and NaHCO$_3$ (aqueous), dried (Na$_2$SO$_4$) and evaporated in vacuo. Column chromatography (SiO$_2$: MeOH/DCM, 5:95) gave the title compound as a yellow oil (129 mg). δH (DMSO-d$^6$) (mixture of diastereoisomers) 8.23 (1H, d, J 8.7 Hz, CONH), 8.00 (t, J 1.9 Hz) and 7.98 (t, J 1.9 Hz) together (1H, Cl$_2$ArH), 7.85 (d, J 1.9 Hz) and 7.79 (d, J 1.9HZ) together (2H, Cl$_2$ArH$_2$), 6.99 (d, J 8.4 Hz) and 6.94 (d, J 8.4 Hz) together (2H, ArH), 6.48–6.42 (2H, m, ArH), 5.05–4.93 (3H, m, CHα+NH$_2$), 5.67 (d, J 5.7 Hz) and 5.62 (d, J 6.1 Hz) together (1H, OH), 4.4–4.3 (1H, m, C$\underline{H}$NH), 4.27–4.19 (1H, m, C$\underline{H}$OH), 4.06–3.98 (2H, m, CO$_2$C$\underline{H}_2$CH$_3$), 3.40–3.20 (2H, m, CH$_2$N), 1.9–01.55 (4H, m, CHC$\underline{H}_2$C$\underline{H}_2$CH$_2$N), 1.15 (t, J 7.1 HZ) and 1.14 (t, J 7.1 Hz) together (3H, CO$_2$CH$_2$C$\underline{H}_3$); m/z (ES$^+$, 70V) 552 (MH$^+$).

EXAMPLE 19

Ethyl (2RS,3RS)-3-{4[(3,5-dichloroisonicotinoyl) amino]phenyl}-3-{[((2S)-1-[(3,5-dichlorophenyl) sulphonyl]tetrahydro-1-H-pyrrol-2-yl)carbonyl] amino}-2-hydroxypropanoate A solution of 3,5-dichloroisonicotinoyl chloride (55 mg, 0.259 mmol) in DCM (2 ml) was added to a solution of the compound of Example 18 (125 mg, 0.236 mmol) and NMM (28 µl, 0.259 mmol) in DCM (5 ml). The mixture was stirred overnight at room temperature then diluted with DCM, washed with dilute HCl, dried (Na$_2$SO$_4$) and evaporated in vacuo. Column chromatography (SiO$_2$: MeOH/DCM, 6:94) gave the title compound as a yellow foam (135 mg). δH (DMSO-d$^6$) (mixture of diastereoisomers) 10.88 (1H, s, CONH), 8.78 (2H, s, Cl$_2$PyH$_2$), 8.50 (1H, app. t. J 9.1 Hz, CONH), 8.01 (t, J 1.9 Hz) and 7.97 (t, J 1.9 Hz) together (1H, Cl$_2$ArH), 7.84 (d, J 1.9 Hz) and 7.77 (d, J 1.9 Hz) together (2H, Cl$_2$ArH$_2$), 7.58 (d, J 8.6 Hz) and 7.55 (d, J 8.5 Hz) together (2H, ArH), 7.35 (d, J 8.6 Hz) and 7.30 (d, J 8.6 Hz) together (2H, ArH), 5.89 (d, J 5.9 Hz) and 5.84 (d, J 6.2 Hz) together (1H, OH), 5.14–5.07 (1H, m, CHα), 4.36–4.26 (2H, m, C$\underline{H}$NH+C$\underline{H}$OH), 4.11–4.04 (2H, m, CO$_2$CH$_2$), 3.45–3.20 (2H, m, CH$_2$N), 1.90–1.60 (4H, m, C$\underline{H}_2$C$\underline{H}_2$CH$_2$N), 1.20 (t, J 7.1 Hz) and 1.19 (t, J 7.1 Hz) together (3H, CO$_2$CH$_2$C$\underline{H}_3$).

EXAMPLE 20

(2RS,3RS)-3-{4-[(3,5-Dichloroisonicotinoyl)amino] phenyl}-3-{[((2S)-1-[(3,5-dichlorophenyl)sulphonyl] tetrahydro-1-H-pyrrol-2-yl)carbonyl]amino}-2-hydroxypropanoic acid The title compound was prepared by the method of Example 2 from the compound of Example 19 as a pale brown solid. δH (DMSO-d$^6$) (mixture of diastereoisomers) 12.7 (1H, br s, CO$_2$H), 10.87 (1H, s, CONH), 8.78 (2H, s, Cl$_2$PyH$_2$), 8.50 (d, J 8.9 Hz) and 8.45 (d, J 8.8 Hz) together (1H, CONH), 8.01 (t, J 1.9 Hz) and 7.96 (t, J 1.9 Hz) together (1H, Cl$_2$ArH), 7.86 (d, J 1.8 Hz) and 7.78 (d, J 1.9 Hz) together (2H, Cl$_2$ArH$_2$), 7.58–7.53 (2H, m ArH), 7.35 (d, J 8.7 Hz) and 7.31 (d, J 8.6 Hz) together (2H, ArH), 5.64 (1H, br m, OH), 5.16–5.09 (1H, m, CHα), 4.42–4.20 (2H, m, C$\underline{H}$OH+C$\underline{H}$NH), 3.50–3.20 (2H, m, C$\underline{H}_2$N), 1.90–1.60 (4H, m, C$\underline{H}_2$C$\underline{H}_2$CH$_2$N); m/z (ES$^+$, 70V) 677 (MH$^+$).

EXAMPLE 21

3-({[(4S)-3-Acetyl-1,3-thiazolan-4-yl] carbonyl}amino)-3-{4-[(3,5-dichloroisonicotinoyl) amino]phenyl}propanoic acid Prepared from Intermediate 6 and N-Acetyl-D-thioproline by the methods described in Examples 18 and 2. δH (DMSO-d$^6$, 390K) (mixture of diastereoisomers) 10.41 (1H, s, CONH), 8.69 (2H, S, Cl$_2$PyH$_2$) 7.99 (1H, br s, CONH), 7.59–7.57 (2H, m, ArH), 7.38–7.34 (2H, m, ArH), 5.26–5.21 (1H, m, CHα), 4.87–4.78 (2H, m, C$\underline{H}$NH+NC$\underline{H}_A$H$_B$S), 4.49–4.44 (1H, m, NCH$_A$$\underline{H}_B$S), 3.35–3.30 (m) and 3.20–3.08 (m) and 2.87–2.64 (m) together (4H, m, CH C$\underline{H}_2$S+C$\underline{H}_2$CO$_2$H), 2.51 (s) and 2.50 (s) together (3H, COCH$_3$); m/z (ES$^+$, 70V) 511 (MH$^+$).

EXAMPLE 22

3-({[(4R)-3-Acetyl-1,3-thiazolan-4-yl] carbonyl}amino)-3-{4-[3,5-dichloroisonicotinoyl) amino]phenyl}propanoic acid Prepared from intermediate 6 and N-acetyl-L-thioproline by the methods described in Examples 18 and 2. δH (DMSO-d$^6$, 390K) (mixture of diastereoisomers) 10.41 (1H, s, CONH), 8.69 (2H, s, Cl$_2$PyH$_2$), 7.99 (1H, br s, CONH), 7.59–7.57 (2H, m, ArH), 7.38–7.34 (2H, m, ArH), 5.26–5.21 (1H, m, CHα), 4.87–4.78 (2H, m, C$\underline{H}$NH+NC$\underline{H}_A$H$_B$S), 4.49–4.44 (1H, m, NCH$_A$$\underline{H}_B$S), 3.35–3.30 (m) and 3.20–3.08 (m) and 2.87–2.64 (m) together (4H, m, CH C$\underline{H}_2$S+C$\underline{H}_2$CO$_2$H), 2.51 (s) and 2.50 (s) together (3H, COCH$_3$); m/z (ES$^+$, 70V) 511 (MH$^+$).

EXAMPLE 23

3-[4-[(2,6-Dichlorobenzoyl)amino]phenyl]-3-[(cyclohexlcarbonyl)amino]propanoic acid To Intermediate 14 (130 mg) was added DMF (0.5 ml), DIEA in DMF (1M, 0.2 ml), cyclohexanecarboxylic acid in DMF (1M, 0.3 ml) and [O-(7-azabenzotriazol-1-yl)-1,1,3,3-tetramethyluronium]hexafluorophosphate in DMF (0.5M, 0.5 ml). The solution was agitated at room temperature for 10 h followed by filtration and multiple washes with DMF and DCM.

The resin was treated with a mixture of TFA, DCM and water (6:3:1) (3 ml) for 3 h with agitation and then filtered. The filtrate was evaporated in vacuo to give the crude product which was purified by preparative HPLC to afford the title compound (2 mg)

HPLC-MS Retention time 3.9 min; m/z (ES$^+$, 70V) 464 (MH$^+$).

HPLC-MS

HPLC-MS was performed on a Hewlett Packard 1100/MSD ES Single Quadrapole system with diode array detector using a Luna C$_{18}$(2) 50×4.6 mm (3 µm particle size) column, running a gradient of 95% [20 mM ammonium formate, pH 3.5], 5% [0.1% formic acid in acetonitrile] to 10% [20 mM ammonium formate, pH 3.5], 90% (0.1% formic acid in acetonitrile] over 3 min, then maintaining the mobile phase at that ratio for a further 2 min. Flow rate 0.8 ml/min.

The compounds of Examples 24 to 27 were prepared in a similar manner to the compound of Example 23, using Intermediate 14 and the carboxylic acid shown.

EXAMPLE 24

3-{4-[(2,6-Dichlorobenzoyl)amino]phenyl}-3-{[2-(3-pyridinyl)acetyl]amino}propanoic acid 3-Pyridylacetic acid gave the title compound (4 mg)

HPLC-MS Retention time 3.2 min; m/z (ES$^+$, 70V) 472 (MH$^+$).

EXAMPLE 25

3-{4-[(2,6-Dichlorobenzoyl)amino]phenyl}-3-[({2-[(2,5-dimethoxyphenyl)thio]-3-pyridinyl}carbonyl) amino]propanoic acid 2-(2,5-Dimethoxyphenylthio)-3-pyridine carboxylic acid gave the title compound (5 mg)

HPLC-MS Retention time 3.9 min; m/z (ES$^+$, 70V) 626 (MH$^+$).

EXAMPLE 26

3-{4-[(2,6-Dichlorobenzoyl)amino]phenyl}-3-[(3,3-dimethylbutanoyl)amino]propanoic acid 3,3-Dimethylbutanoic acid gave the title compound (2 mg)

HPLC-MS Retention time 3.9 min; m/z (ES$^+$, 70V) 451 (MH$^+$).

The compounds of Examples 27–47 were prepared in a similar manner to the compound of Example 23 using Intermediate 13 and the starting material shown.

EXAMPLE 27

3-{4-[(3,5-Dichloroisonicotinoyl)amino]phenyl}-3-[({2-[(2,5-dimethoxyphenyl)thio]-3-pyridinyl}carbonyl)amino]propanoic acid 2-(2,5-dimethoxyphenylthio)-3-pyridine carboxylic acid gave the title compound (4 mg)

HPLC-MS Retention time 3.7 min; m/z (ES$^+$, 70V) 627 (MH$^+$).

EXAMPLE 28

3-{4-[(3,5-Dichloroisonicotinoyl)amino]phenyl}-3-{[(2-chloro-3-pyridinyl)carbonyl]amino}propanoic acid 2-Chloronicotinic acid gave the title compound (7 mg)

HPLC-MS Retention time 3.4 min; m/z (ES$^+$, 70V) 493 (MH$^+$).

EXAMPLE 29

3-{4-[(3,5-Dichloroisonicotinoyl)amino]phenyl}-3-({[1-(4-chlorophenyl)cyclopentyl]carbonyl}amino)propanoic acid 1-(4-Chlorophenyl)-1-cyclopentanecarboxylic acid gave the title compound (3 mg)

HPLC-MS Retention time 4.3 min; m/z (ES$^+$, 70V) 560 (MH$^+$).

EXAMPLE 30

3-{4-[(3,5-Dichloroisonicotinoyl)amino]phenyl}-3-{[(E)-3-phenyl-2-propenoyl]amino)propanoic acid trans-Cinnamic acid gave the title compound (4 mg)

HPLC-MS Retention time 3.8 min; m/g (ES$^+$, 70V) 484 (MH$^+$).

EXAMPLE 31

3-{4-[(3,5-Dichloroisonicotinoyl)amino]phenyl}-3-[(4-phenylbutanoyl)amino]propanoic acid 4-Phenylbutanoic acid gave the title compound (3 mg)

HPLC-MS Retention time 3.8 min; m/z (ES$^+$, 70V) 500 (MH$^+$).

EXAMPLE 32

3-{4-[(3,5-Dichloroisonicotinoyl)amino]phenyl}-3-[(4-piperidinylcarbonyl)amino]propanoic acid Isonipecotic acid gave the title compound (3 mg)

HPLC-MS Retention time 2.9 min; m/z (ES$^+$, 70V) 465 (MH$^+$).

EXAMPLE 33

3-{4-[(3,5-Dichloroisonicotinoyl)amino]phenyl}-3-{[(4,6-dimethyl-2-oxo-2H-pyran-5-yl)carbonyl]amino}propanoic acid Isodehydracetic acid gave the title compound (2 mg)

HPLC-MS Retention time 3.4 min; m/z (ES$^+$, 70V) 504 (MH$^+$).

EXAMPLE 34

3-{4-[(3,5-Dichloroisonicotinoyl)amino]phenyl}-3-[(cyclobutylcarbonyl)amino]propanoic acid Cyclobutanecarboxylic acid gave the title compound (1 mg)

HPLC-MS Retention time 3.6 min; m/z (ES$^+$, 70V) 436 (MH$^+$).

EXAMPLE 35

3-{4-[(3,5-Dichloroisonicotinoyl)amino]phenyl}-3-[(cyclopropylcarbonyl)amino]propanoic acid Cyclopropanecarboxylic acid gave the title compound (1 mg)

HPLC-MS Retention time 3.5 min; m/z (ES$^+$, 70V) 422 (MH$^+$).

EXAMPLE 36

3-{4-[(3,5-Dichloroisonicotinoyl)amino]phenyl}-3-{[(3-methylcyclohexyl)carbonyl]amino}propanoic acid 3-Methyl-1-cyclohexanecarboxylic acid gave the title compound (2 mg)

HPLC-MS Retention time 4.0 min; m/z (ES$^+$, 70V) 478 (MH$^+$).

EXAMPLE 37

3-{4-[(3,5-Dichloroisonicotinoyl)amino]phenyl}-3-{[(4-methylcyclohexyl)carbonyl]amino}propanoic acid 4-Methyl-1-cyclohexanecarboxylic acid gave the title compound (2 mg)

HPLC-MS Retention time 4.0 min; m/z (ES$^+$, 70V) 478 (MH$^+$).

EXAMPLE 38

3-{4-[(3,5-Dichloroisonicotinoyl)amino]phenyl}-3-[(3,3-dimethylbutanoyl)amino]propanoic acid 3,3-Dimethylbutanoic acid gave the title compound (5 mg)

HPLC-MS Retention time 3.7 min; m/z (ES$^+$, 70V) 452 (MH$^+$).

EXAMPLE 39

3-{4-[(3,5-Dichloroisonicotinoyl)amino]phenyl}-3-({[5-(2-pyrazinyl)-1,3-thiazol-2-yl]carbonyl}amino)propanoic acid 5-(2-Pyrazinyl)-2-thiazolylcarboxylic acid gave the title compound (2 mg)

HPLC-MS Retention time 3.7 min; m/z (ES$^+$, 70V) 453 (MH$^+$).

EXAMPLE 40

3-{4-[(3,5-Dichloroisonicotinoyl)amino]phenyl}-3-
{[(1-methyl-5-nitro-1H-pyrazo-4-yl)carbonyl]
amino}propanoic acid 1-Methyl-5-nitropyrazole-4-carboxylic acid gave the title compound (3 mg)

HPLC-MS Retention time 3.6 min; m/z (ES$^+$, 70V) 507 (MH$^+$).

EXAMPLE 41

3-{4-[(3,5-Dichloroisonicotinoyl)amino]phenyl}-3-
{[(4-methyl-1,2,3-thiadiazol-5-yl)carbonyl]
amino}propanoic acid 4-Methyl-1,2,3-thiadiazole-5-carboxylic acid gave the title compound (3 mg)

HPLC-MS Retention time 3.6 min; m/z (ES$^+$, 70V) 480 (MH$^+$).

EXAMPLE 42

3-{4-[(3,5-Dichloroisonicotinoyl)amino]phenyl}-3-
[(2,1,3-benzoxadiazol-4-ylcarbonyl)amino]
propanoic acid Benzofurazan-5-carboxylic acid gave the title compound (3 mg)

HPLC-MS Retention time 3.8 min; m/z (ES$^+$, 70V) 500 (MH$^+$).

EXAMPLE 43

3-{4-[(3,5-Dichloroisonicotinoyl)amino]phenyl}-3-
{[(1-ethyl-3-methyl-1H-pyrazol-5-yl)carbonyl]
amino}propanoic acid 1-Ethyl-3-methyl-1H-pyrazole-5-carboxylic acid gave the title compound (3 mg)

HPLC-MS Retention time 3.6 min; m/z (ES$^+$, 70V) 490 (MH$^+$).

EXAMPLE 44

3-{4-[(3,5-Dichloroisonicotinoyl)amino]phenyl}-3-
{[(1-phenylcyclopropyl)carbonyl]amino}propanoic
acid 1-Phenyl-1-cyclopropanecarboxylic acid gave the title compound (4 mg)

HPLC-MS Retention time 3.9 min; m/z (ES$^+$, 70V) 498 (MH$^+$).

EXAMPLE 45

3-{4-[(3,5-Dichloroisonicotinoyl)amino]phenyl}-3-
({[1-(4-chlorophenyl)cyclopentyl]carbonyl}amino)
propanoic acid 1-(4-Chlorophenyl)-1-cyclopropanecarboxylic acid gave the title compound (5 mg)

HPLC-MS Retention time 4.1 min; m/z (ES$^+$, 70V) 532(MH$^+$).

EXAMPLE 46

3-{4-[(3,5-Dichloroisonicotinoyl)amino]phenyl}-3-
(propanoylamino)propanoic acid Propanoic acid gave the title compound (2 mg)

HPLC-MS Retention time 3.4 min; m/z (ES$^+$, 70V) 410 (MH$^+$).

EXAMPLE 47

3-{4-[(3,5-Dichloroisonicotinoyl)amino]phenyl}-3-
{[2-(3-pyridinyl)acetyl]amino}propanoic acid 3-Pyridylacetic acid gave the title compound (3 mg)

HPLC-MS Retention time 3.1 min; m/z (ES$^+$, 70V) 473 (MH$^+$).

EXAMPLE 48

3-(4-{[(2,5-Dichlorophenyl)sulphonyl]
amino}phenyl)-3-[(3,5-dichloroisonicotinoyl)
amino}propanoic acid To Intermediate 12 (200 mg) was added 2,5-dichlorobenzenesulfonyl chloride (98 mg, 0.4 mmol) in pyridine (10 ml). The solution was agitated at room temperature for 12 h followed by filtration and multiple washes with DMF and DCM. The resin was treated with a 20% solution of piperidine in DMF (10 ml) for 30 min at room temperature then filtered and washed as before.

To this resin was added DIEA (70 µl, 0.4 mmol) and 3,5-dichloroisonicotinoyl chloride (84 µl, 0.4 mmol) in DCM (10 ml) and the solution agitated for 12 h at room temperature followed by filtration and washes with DMF and DCM. The resin was treated with a 60% solution of TFA in DCM (5 ml) for 3 h with agitation at room temperature and then filtered. The filtrate was evaporated in vacuo to give the crude product which was purified by preparative HPLC to afford the title compound (3 mg).

HPLC-MS Retention time 3.9 min; m/z (ES$^+$, 70V) 563 (MH$^+$).

EXAMPLE 49

3-{4-[(3,5-Dichloroisonicotinoyl)amino]phenyl}-3-
{[(3,4-dichloroanilino)carbonyl]amino}propanoic
acid To Intermediate 12 (200 mg) was added DIEA (70 µl, 0.4 mmol) and 3,5-dichloronicotinoyl chloride (70 µl, 0.4 mmol) in DCM (10 ml). The solution was agitated at room temperature for 12 h followed by filtration and multiple washes with DMF and DCM. The resin was treated with a 20% solution of piperidine in DMF (10 ml) for 30 min at room temperature then filtered and washed as before.

To this resin was added DIEA (70 µl, 0.4 mmol) and 3,4-dichlorophenylisocyanate (75 mg) 0.4 mmol) in DCM (10 ml) and the solution agitated for 12 h at room temperature followed by filtration and washed with DMF and DCM.

The resin was treated with a 60% solution of TFA in DCM (5 ml) for 3 h with agitation at room temperature and then filtered. The filtrate was evaporated in vacuo to give the crude product which was purified by preparative HPLC to afford the title compound (2 mg)

HPLC-MS Retention time 4.7 min; m/z (ES$^+$, 70V) 542 (MH$^+$).

EXAMPLE 50

3-(4-{[(3,4-Dichloroanilino)carbonyl]
amino}phenyl)-3-[(3,5-dichloroisonicotinoyl)
amino}propanoic acid To Intermediate 12 (200 mg) was added DIEA (70 µl, 0.4 mmol) and 3,4-dichlorophenylisocyanate (75 mg, 0.4 mmol) in DCM (10 ml) and the solution agitated for 12 h at room temperature followed by filtration and washes with DMF and DCM. The resin was treated with a 20% solution of piperidine in DMF (10 ml) for 30 min at room temperature then filtered and washed as before.

To this resin was added DIEA (70 µl, 0.4 mmol) and 3,5-dichloronicotinoyl chloride (84 µl, 0.4 mmol) in DCM (10 ml) and the solution agitated for 12 h at room temperature followed by filtration and washes with DMF and DCM.

The resin was treated with a 60% solution of TFA in DCM (5 ml) for 3 h with agitation at room temperature and then filtered. The filtrate was evaporated in vacuo to give the crude product which was purified by preparative HPLC to afford the title compound (5 mg)

HPLC-MS Retention time 4.1 min; m/z (ES$^+$, 70V) 542 (MH$^+$).

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

$\alpha_4\beta_1$ Integrin-dependent Jurkat Cell Adhesion to VCAM-Ig 96 well NUNC plates were coated with F(ab)$_2$ fragment goat anti-human IgG Fcγ-specific antibody [Jackson Immuno Research 109-006-098: 100 µl at 2 µg/ml in 0.1M NaHCO$_3$, pH 8.4], overnight at 4°. The plates were washed (3×) in phosphate-buffered saline (PBS) and then blocked for 1 h in PBS/1% BSA at room temperature on a rocking platform. After washing (3× in PBS) 9 ng/ml of purified 2d VCAM-Ig diluted in PBS/1% BSA was added and the plates left for 60 minutes at room temperature on a rocking platform. The plates were washed (3× in PBS) and the assay then performed at 37° for 30 min in a total volume of 200 µl containing 2.5×10$^5$ Jurkat cells in the presence or absence of titrated test compounds.

Each plate was washed (2×) with medium and the adherent cells were fixed with 100 µl MeOH for 10 minutes followed by another wash. 100 µl 0.25% Rose Bengal (Sigma R4507) in PBS was added for 5 minutes at room temperature and the plates washed (3×) in PBS. 100 µl 50% (v/v) EtOH in PBS was added and the plates left for 60 min after which the absorbance (570 nm) was measured.

$\alpha_4\beta_7$ Integrin-dependent JY Cell Adhesion to MAdCAM-Ig

This assay was performed in the same manner as the $\alpha_4\beta_1$ assay except that MAdCAM-Ig (150 ng/ml) was used in place of 2d VCAM-Ig and a sub-line of the β-lympho blastoid cell-line JY was used in place of Jurkat cells. The IC$_{50}$ value for each test compound was determined as described in the $\alpha_4\beta_1$ integrin assay.

$\alpha_5\beta_1$ Integrin-dependent K562 Cell Adhesion to Fibronectin 96 well tissue culture plates were coated with human plasma fibronectin (Sigma F0895) at 5 µg/ml in phosphate-buffered saline (PBS) for 2 hr at 37° C. The plates were washed (3× in PBS) and then blocked for 1 h in 100 µl PBS/1% BSA at room temperature on a rocking platform. The blocked plates were washed (3× in PBS) and the assay then performed at 37° C. in a total volume of 200 µl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the $\alpha_4\beta_1$ assay above.

$\alpha_m\beta_2$-Dependent Human Polymorphonuclear Neutrophils Adhesion to Plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 µl in the presence of 10 ng/ml phorbol-12-myristate-13-acetate, and in the presence or absence of test compounds, and incubated for 20 min at 37° C. followed by 30 min at room temperature. The plates were washed in medium and 100 µl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50 µg/ml TMB (Boehringer Mannheim) in 0.1M sodium acetate/citrate buffer, pH 6.0 and absorbance measured at 630 nm.

αIIb/β$_3$-Dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 µM ADP (Sigma) in the presence or absence of inhibitors.

In the above assays the preferred compounds of the invention generally have IC$_{50}$ values in the $\alpha_4\beta_1$ and $\alpha_4\beta_7$ assays of 1 µM and below. In the other assays featuring α integrins of other subgroups the same compounds had IC$_{50}$ values of 50 µM and above thus demonstrating the potency and selectivity of their action against $\alpha_4$ integrins.

What is claimed is:

1. A compound of formula (1):

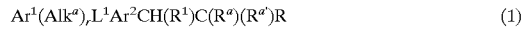

wherein

Ar$^1$ is an aromatic or C$_{1-9}$ heteroaromatic group containing one to four heteroatoms selected from oxygen, nitrogen, and sulfur, and is optionally substituted with one or more atoms or groups -L$^2$(Alk)$_t$L$^3$ (R$^4$)$_u$;

L$^2$ and L$^3$, which may be the same or different, is each a covalent bond or a divalent linker atom or group selected from —O—, —S—, —C(O)—, —C(O)O—, —OC(O)—, —C(S)—, —S(O)—, —S(O)$_2$—, —N(R$^8$)—, —CON(R$^8$)—, —OC(O)N(R$^8$)—, —CSN(R$^8$)—, —N(R$^8$)CO—, —N(R$^8$)C(O)O—, —N(R$^8$)CS—, —S(O)$_2$N(R$^8$)—, —N(R$^8$)S(O)$_2$—, —N(R$^8$)CON(R$^8$)—, —N(R$^8$)CSN(R$^8$)—, and —N(R$^8$)SO$_2$N(R$^8$)—;

R$^8$ is a hydrogen atom or a C$_{1-6}$alkyl group optionally substituted with one or more halogen atoms, hydroxy groups, or C$_{1-6}$alkoxy groups;

t is zero or the integer 1;

u is an integer 1, 2 or 3;

Alk is an aliphatic or heteroaliphatic chain;

R$^4$ is a hydrogen or halogen atom or a group selected from C$_{1-6}$alkyl, —OR$^5$, —SR$^5$, —NR$^5$R$^6$, —NO$_2$, —CN, —CO$_2$R$^5$, —SO$_3$H, —SO$_3$R$^5$, —SOR$^5$, —SO$_2$R$^5$, —OCO$_2$R$^5$, —CONR$^5$R$^6$, —OCONR$^5$R$^6$, —CSNR$^5$R$^6$, —COR$^5$, —OCOR$^5$, —N(R$^5$)COR$^6$, —N(R$^5$)CSR$^6$, —SO$_2$N(R$^5$)(R$^6$), —N(R$^5$)SO$_2$R$^6$, —N(R$^5$)CON(R$^6$)$^7$), —N(R$^5$)CSN(R$^6$)(R$^7$), and —N(R$^5$)SO$_2$N(R$^6$)(R$^7$); and $R^5$, $R^6$, and $R^7$, which may be the same or different, is each a hydrogen atom or a straight or branched $C_{1-6}$alkyl group optionally substituted with one or more halogen atoms, hydroxy groups, or $C_{1-6}$alkoxy groups; provided that when t is zero and each of $L^2$ and $L^3$ is a covalent bond, then u is the integer 1 and $R^4$ is other than a hydrogen atom;

$L^1$ is a covalent bond or a linker atom or group selected from —CON($R^2$)—, —S(O)$_2$N($R^2$)—, —N($R^2$)—, and —O—;

$R^2$ is a hydrogen atom or a $C_{1-3}$alkyl group;

$Ar^2$ is a phenylene group optionally substituted with one or two atoms or groups -$L^2$(Alk)$_t$$L^3$($R^4$)$_u$;

$R^1$ is a group selected from —NHCOR$^3$, —NHSO$_2$R$^3$, —NHR$^3$, —NHC(O)OR$^3$, —NHCSR$^3$, —NHCON($R^3$)($R^{3a}$), —NHSO$_2$N($R^3$)($R^{3a}$), and —NHCSN($R^3$)($R^{3a}$);

$R^3$ is an optionally substituted $C_{3-10}$ cycloaliphatic group, an optionally substituted $C_{7-10}$ polycycloaliphatic group, an optionally substituted $C_{3-10}$ heterocycloaliphatic group containing one, two, three or four heteroatoms or heteroatom-containing groups selected from —O—, —S—, —C(O)—, —C(O)O—, OC(O)—, —C(S)—, —S(O)—, —S(O)$_2$—, —N($R^8$)—, —C(O)N$R^8$—, —OC(O)N($R^8$)—, —CSN($R^8$)—, —N($R^8$)CO—, —N($R^8$)C(O)O—, —N($R^8$)CS—, —S(O)$_2$N($R^8$)—, —N($R^8$)S(O)$_2$—, —N($R^8$)CON($R^8$)—, —N($R^8$)CSN($R^8$)— and —N($R^8$)SO$_2$N($R^8$)—; an optionally substituted $C_{7-10}$ heteropolycycloaliphatic group containing one, two, three or four heteroatoms or heteroatom-containing groups selected from —O—, —S—, —C(O)—, —C(O)O—, OC(O)—, —C(S)—, —S(O)—, —S(O)$_2$—, —N($R^8$)—, —C(O)NR$^8$—, —OC(O)N($R^8$)—, —CSN($R^8$)—, —N($R^8$)CO—, —N($R^8$)C(O)O—, —N($R^8$)CS—, —S(O)$_2$N($R^8$)—, —N($R^8$)S(O)$_2$—, —N($R^8$)CON($R^8$)—, —N($R^8$)CSN($R^8$)— and —N($R^8$)SO$_2$N($R^8$)—; an optionally substituted aromatic group, or an optionally substituted $C_{1-9}$ heteroaromatic group containing one, two, three or four heteroatoms selected from oxygen, nitrogen, and sulfur;

$R^{3a}$ is a hydrogen atom, an optionally substituted $C_{1-6}$ aliphatic group, an optionally substituted $C_{1-6}$ heteroaliphatic group containing one, two, three or four heteroatoms or heteroatom-containing groups selected from —O—, —S—, —C(O)—, —C(O)O—, OC(O)—, —C(S)—, —S(O)—, —S(O)$_2$—, —N($R^8$)—, —C(O)NR$^8$—, —OC(O)N($R^8$)—, —CSN($R^8$)—, —N($R^8$)CO—, —N($R^8$)C(O)O—, —N($R^8$)CS—, —S(O)$_2$N($R^8$)—, —N($R^8$)S(O)$_2$—, —N($R^8$)CON($R^8$)—, —N($R^8$)CSN($R^8$)— and —N($R^8$)SO$_2$N($R^8$)—, an optionally substituted $C_{3-10}$ cycloaliphatic group, an optionally substituted $C_{7-10}$ polycycloaliphatic group, an optionally substituted $C_{3-10}$ heterocycloaliphatic group containing one, two, three or four heteroatoms or heteroatom-containing groups selected from —O—, —S—, —C(O)—, —C(O)O—, OC(O)—, —C(S)—, —S(O)—, —S(O)$_2$—, —N($R^8$)—, —C(O)NR$^8$—, —OC(O)N($R^8$)—, —CSN($R^8$)—, —N($R^8$)CO—, —N($R^8$)C(O)O—, —N($R^8$)CS—, —S(O)$_2$N($R^8$)—, —N($R^8$)S(O)$_2$—, —N($R^8$)CON($R^8$)—, —N($R^8$)CSN($R^8$)— and —N($R^8$)SO$_2$N($R^8$)—; an optionally substituted $C_{7-10}$ heteropolycycloaliphatic group containing one, two, three or four heteroatoms or heteroatom-containing groups selected from —O—, —S—, —C(O)—, —C(O)O—, OC(O)—, —C(S)—, —S(O)—, —S(O)$_2$—, —N($R^8$)—, —C(O)NR$^8$—, —OC(O)N($R^8$)—, —CSN($R^8$)—, —N($R^8$)CO—, —N($R^8$)C(O)O—, —N($R^8$)CS—, —S(O)$_2$N($R^8$)—, —N($R^8$)S(O)$_2$—, —N($R^8$)CON($R^8$)—, —N($R^8$)CSN($R^8$)— and —N($R^8$)SO$_2$N($R^8$)—; an optionally substituted aromatic group, or an optionally substituted $C_{1-9}$ heteroaromatic group containing one, two, three or four heteroatoms selected from oxygen, nitrogen, and sulfur;

wherein the optional substituents for the aromatic groups and the heteroaromatic groups of $R^3$ and $R^{3a}$ are selected from one or more atoms or groups $R^{13}$ wherein $R^{13}$ is —$R^{13a}$ or -Alk$^4$($R^{3a}$)$_m$;

$R^{13a}$ is a halogen atom, or an amino, substituted amino, nitro, cyano, amidino, hydroxyl, substituted hydroxyl, formyl, carboxyl, esterified carboxyl, thiol, substituted thiol, —COR$^{14}$; —CSR$^{14}$, —SO$_3$H, —SOR$^{14}$, —SO$_2$R$^{14}$, —SO$_2$NH$_2$, —SO$_2$NHR$^{14}$, —SON$_2$(R$^{14}$)$_2$, —CONH$_2$, —CSNH$_2$, —CONHR$^{14}$, —CSNHR$^{14}$, —CON(R$^{14}$)$_2$, —CSN(R$^{14}$)$_2$, —N(R$^{11}$)SO$_2$R$^{14}$, —N(SO$_2$R$^{14}$)$_2$, —N(R$^{11}$)SO$_2$NH$_2$, —N(R$^{11}$)SO$_2$NHR$^{14}$, —N(R$^{11}$)SO$_2$N(R$^{14}$)$_2$, —N(R$^{11}$)COR$^{14}$, —N(R$^{11}$)CONH$_2$, —N(R$^{11}$)CONHR$^{14}$, —N(R$^{11}$)CON(R$^{14}$)$_2$, —N(R$^{11}$)CSNH$_2$, —N(R$^{11}$)CSNHR$^{14}$, —N(R$^{11}$)CSN(R$^{14}$)$_2$, —N(R$^{11}$)CSR$^{14}$, —N(R$^{11}$)C(O)OR$^{14}$, —SO$_2$NHet$^1$, —CONHet$^1$, —CSNHet$^1$, —N(R$^{11}$)SO$_2$NHet$^1$, —N(R$^{11}$)CONHet$^1$, —N(R$^{11}$)CSNHet$^1$, —SO$_2$N(R$^{11}$)Het$^2$, -Het$^2$, —CON(R$^{11}$)Het$^2$, —CSN(R$^{11}$)Het$^2$, —N(R$^{11}$)CON(R$^{11}$)Het$^2$, —N(R$^{11}$)CSN(R$^{11}$)Het$^2$, aryl or heteroaryl group;

$R^{14}$ is an -Alk$^4$($R^{13a}$)$_m$, aryl or heteroaryl group;

NHet$^1$ is a $C_{5-7}$cyclicamino group optionally containing one or more —O— or —S— atoms or —N(R$^{11}$)—, —C(O)— or —C(S)— groups and optionally substituted with one or more substituents as defined for the cycloaliphatic groups of $R^3$ and $R^{3a}$;

Het$^2$ is a monocyclic $C_{5-7}$carbocyclic group optionally containing one or more —O— or —S— atoms or —N(R$^{11}$)—, —C(O) or —C(S)— groups and optionally substituted with one or more substituents as defined for the cycloaliphatic groups of $R^3$ and $R^{3a}$;

Alk$^4$ is a straight or branched $C_{1-6}$alkylene, $C_{2-6}$alkenylene or $C_{2-6}$alkynylene chain, optionally interrupted by one, two, or three —O— or —S— atoms or —S(O), or —N(R$^{15}$)— groups;

$R^{15}$ is a hydrogen atom or $C_{1-6}$alkyl group;

m is zero or an integer 1, 2 or 3;

n is an integer 1 or 2;

wherein the optional substituents for the aliphatic groups and the heteroaliphatic groups of $R^{3a}$ are selected from halogen atoms, hydroxy groups, $C_{1-6}$alkoxy groups, thiol groups, $C_{1-6}$alkylthio groups, amino groups, and substituted amino groups;

wherein the optional substituents for the cycloaliphatic, polycycloaliphatic, heterocycloaliphatic and heteropolycycloaliphatic groups of $R^3$ and $R^{3a}$ are selected from halogen atoms, $C_{1-6}$alkyl groups, haloC$_{1-6}$alkyl groups optionally substituted with hydroxyl groups, hydroxyl groups, $C_{1-6}$alkoxy groups, haloC$_{1-6}$alkoxy groups, thiol groups, $C_{1-6}$alkylthio groups, aromatic groups, heteroaromatic groups, and -(Alk$^2$)$_v$R$^{10}$ groups;

Alk$^2$ is a straight or branched $C_{1-3}$ alkylene chain;

v is zero or an integer 1;

$R^{10}$ is a —OH, —SH, —N($R^{11}$)$_2$, —CN, —CO$_2$$R^{11}$, —NO$_2$, —CON($R^{11}$)$_2$, —CSN($R^{11}$)$_2$, —OC(O)N ($R^{11}$)$_2$, —C(O)H, —COR$^{11}$, —OCO$_2$$R^{11}$, —OC(O) $R^{11}$, —C(S)$R^{11}$, —CSN($R^{11}$)$_2$, —N($R^{11}$)COR$^{11}$, —N($R^{11}$)CSR$^{11}$, —SO$_3$H, —SOR$^{11}$, —SO$_2$$R^{11}$, —SO$_3$$R^{11}$, —SO$_2$N($R^{11}$)$_2$, —N($R^{11}$)SO$_2$$R^{11}$, —N($R^{11}$) CON($R^{11}$)$_2$, —N($R^{11}$)CSN($R^{11}$)$_2$, or —N($R^{11}$)SO$_2$N ($R^{11}$)$_2$ group; and $R^{11}$ is an atom or group as defined for $R^8$ or an optionally substituted cycloaliphatic or hetercycloaliphatic group as defined for $R^3$;

and when $R^3$ is a heterocycloaliphatic group containing one or more nitrogen atoms each nitrogen atom is optionally substituted with a group -(L$^5$)$_p$(Alk$^3$)$_q$$R^{12}$;

L$^5$ is —C(O)—, —C(O)O—, —C(S)—, —S(O)—, —S(O)$_2$—, —CON($R^{11}$)—, —CSN($R^{11}$)—, —SON ($R^{11}$)— or —SO$_2$N($R^{11}$)—;

p is zero or an integer 1;

Alk$^3$ is an optionally substituted aliphatic or heteroaliphatic chain;

q is zero or an integer 1;

$R^{12}$ is a hydrogen atom or an optionally substituted cycloaliphatic, heterocycloaliphatic, polycycloaliphatic, polyheterocycloaliphatic, aromatic or heteroaromatic group;

$R^a$ and $R^{a'}$, which may be the same or different, are each independently selected from a hydrogen or halogen atom or an optionally substituted straight or branched alkyl, alkenyl, alkynyl, haloalkyl, alkoxy, haloalkoxy, alkylthio or -(Alk$^b$)$_m$$R^b$ group (in which Alk$^b$ is a C$_{1-3}$ alkylene chain, m is zero or the integer 1, and $R^b$ is —OH, —SH, —NO$_2$, —CN, —CO$_2$H, —CO$_2$$R^c$ (where $R^c$ is an optionally substituted straight or branched C$_{1-6}$ alkyl group), —SO$_3$H, —SOR$^c$, —SO$_2$$R^c$, —SO$_3$$R^c$, —OCO$_2$$R^c$, —C(O)H, —C(O)$R^c$, —OC(O)$R^c$, —C(S)$R^c$, —NR$^d$R$^e$ (where $R^d$ and $R^e$, which may be the same or different, are each a hydrogen atom or an optionally substituted straight or branched C$_{1-6}$ alkyl group), —CON($R^d$)($R^e$), —OC(O) N($R^d$)($R^e$), —N($R^d$)C(O)$R^e$, —CSN($R^d$)($R^e$), —N($R^d$) C(S)$R^e$, —S(O)$_2$N($R^d$)($R^e$), —N($R^d$)SO$_2$$R^e$, —N($R^d$) CON($R^e$)($R^f$) (where $R^f$ is a hydrogen atom or an optionally substituted straight or branched C$_{1-6}$ alkyl group), —N($R^d$)C(S)N($R^e$)($R^f$) or —N($R^d$)SO$_2$N($R^e$) ($R^f$) group);

Alk$^a$ is an optionally substituted C$_{1-6}$ aliphatic or C$_{1-6}$ heteroaliphatic chain containing one, two, three or four heteroatoms or heteroatom-containing groups selected from —O—, —S—, —C(O)—, —C(O)O—, OC(O)—, —C(S)—, —S(O)—, —S(O)$_2$—, —N($R^8$)—, —C(O)NR$^8$—, —OC(O)N($R^8$)—, —CSN ($R^8$)—, —N($R^8$)CO—, —N($R^8$)C(O)O—, —N($R^8$) CS—, —S(O)$_2$N($R^8$)—, —N($R^8$)S(O)$_2$—, —N($R^8$) CON($R^8$)—, —N($R^8$)CSN($R^8$)—, and —N($R^8$)SO$_2$N ($R^8$)—;

wherein the optional substituents for the aliphatic and heteroaliphatic groups of Alk$^a$ are selected from halogen atoms, hydroxy groups, C$_{1-6}$alkoxy groups, thiol groups, C$_{1-6}$alkylthio groups, amino groups, and substituted amino groups;

r is zero or the integer 1;

R is a carboxylic acid (CO$_2$H), a carboxylic ester group, or carboxylic amide group;

and the salts, hydrates and N-oxides thereof.

2. A compound according to claim 1 in which R is a —CO$_2$H group.

3. A compound according to claim 1 in which $R^{a'}$ is a hydrogen atom.

4. A compound according to claim 1 in which $R^a$ is a hydrogen atom or a hydroxyl group.

5. A compound according to claim 1 in which (Alk$^a$)$_r$L$^1$ is a —CON($R^2$)— group.

6. A compound according to claim 5 in which (Alk$^a$)$_r$L$^1$ is a —CONH— group.

7. A compound according to claim 1 in which Ar$^2$ is a 1,4-phenylene group optionally substituted with one or two atoms or groups -L$^2$(Alk)$_t$L$^3$($R^4$)$_u$.

8. A compound according to claim 7 in which Ar$^2$ is a 1,4-phenylene group.

9. A compound according to claim 1 in which Ar$^1$ is a pyrimidinyl, pyridyl or phenyl group optionally substituted with one or more atoms or groups -L$^2$(Alk)$_t$L$^3$($R^4$)$_u$.

10. A compound according to claim 9 in which Ar$^1$ is a pyridyl or phenyl group optionally substituted with one or more atoms or groups -L$^2$(Alk)$_t$L$^3$($R^4$)$_u$.

11. A compound according to claim 10 in which Ar$^1$ is a 3,5-dichloropyridin-4-yl group.

12. A compound according to claim 1 in which $R^1$ is the group —NHCOR$^3$ or —NHR$^3$.

13. A compound according to claim 12 in which $R^3$ is a pyrrolidinyl or thiazolidinyl group optionally substituted with one or more halogen atoms, C$_{1-6}$alkyl groups, haloC$_{1-6}$ alkyl groups optionally substituted with one or more hydroxyl groups, hydroxyl groups, C$_{1-6}$alkoxy groups, haloC$_{1-6}$alkoxy groups, thiol groups, C$_{1-6}$alkylthio groups, aromatic groups, heteroaromatic groups, or -(Alk$^2$)$_v$$R^{10}$ groups, and each nitrogen atom of the pyrrolidinyl or thiazolidinyl group is optionally substituted with a group -(L$^5$)$_p$(Alk$^3$)$_q$$R^{12}$;

or $R^3$ is a phenyl, pyrimidinyl or 1,3,5-triazinyl group optionally substituted with one or more atoms or groups —$R^{13a}$ or -Alk$^4$($R^{13a}$)$_m$.

14. A compound which is:

3-{4-[(3,5-Dichloroisonicotinoyl)amino]phenyl}-3-({4-[2-hydroxyethylamino]-6-methoxy-1,3,5-triazin-2-yl}amine)propanoic acid;

3-[(3,5-Dichloroisonicotinoyl)amino]-3-{4-[(3,5-dichloroisonicotinoyl)-amino]phenyl}propanoic acid;

3-{4-(3,5-Dichloroisonicotinoyl)amino]phenyl}-3-[(2,6-dimethoxybenzoyl)amino]propanoic acid;

3-({[(4S)-3-Acetyl-1,3-thiazolinan-4-yl]carbonyl}amino-3-{4-[(3,5-dichloroisonicotinoyl)amino] phenyl}propanoic acid;

3-{4-[(3,5-Dichloroisonicotinoyl)amino]phenyl}-3-[({(2S)-1-[(3,5-dichlorophenyl)sulphonyl]tetrahydro-1-H-pyrrol-2-yl}carbonyl)amino]propanoic acid;

(2RS,3RS)-3-{4-[(3,5-Dichloroisonicotinoyl)amino] phenyl}-3-{[((2S)-1-[(3,5-dichlorophenyl)sulphonyl] tetrahydro-1-H-pyrrol-2-yl)carbonyl]amino}-2-hydroxypropanoic acid;

3-{4-[(3,5-Dichloroisonicotinoyl)amino]phenyl}-3-[({2-[(2,5-dimethoxyphenyl)thio]-3-pyridinyl}carbonyl) amino]propanoic acid;

and the salts, hydrates and N-oxides thereof.

15. A pharmaceutical composition comprising a compound according to claim 1 together with one or more pharmaceutically acceptable carriers, excipients or diluents.

16. A method for the treatment of a mammal suffering from inflammatory arthritis, multiple sclerosis, allograft rejection, diabetes, inflammatory dermatoses, asthma or inflammatory bowel disease, comprising administering to the mammal a therapeutically effective amount of a compound according to claim 1.

17. A method according to claim 16 wherein said inflammatory arthritis is selected from the group consisting of rheumatoid arthritis vasculitis and polydermatomyositis.

18. A method according to claim 16 wherein said inflammatory dermatoses are selected from the group consisting of psoriasis and dermatitis.

19. A method for inhibiting, in a mammal, the binding of α4 integrins to the ligands thereof, comprising administering to the mammal an effective amount of a compound according to claim 1.

20. A method according to claim 19 wherein the α4 integrins are selected from the group consisting of α4β1 and α4β7 integrins.

* * * * *